United States Patent [19]
Baker et al.

[11] Patent Number: 6,166,382
[45] Date of Patent: Dec. 26, 2000

[54] METHOD FOR DETERMINING FEED QUALITY

[75] Inventors: Suzanne Kay Baker, Wembley Downs; David Andrew Henry, Joondana; Douglas Barrie Purser, Wembley Downs; Robyn Ann Dynes, Wembley; Brett Steven Wallington, Yangebup, all of Australia

[73] Assignee: Commonwealth Scientific and Industrial Research Organisation, Campbell, Australia

[21] Appl. No.: 09/077,555

[22] PCT Filed: Dec. 2, 1996

[86] PCT No.: PCT/AU96/00776

§ 371 Date: Jun. 9, 1998

§ 102(e) Date: Jun. 9, 1998

[87] PCT Pub. No.: WO97/21091

PCT Pub. Date: Jun. 12, 1997

[30] Foreign Application Priority Data

Dec. 1, 1995 [AU] Australia ................ PN 6928

[51] Int. Cl.$^7$ .................................................. G01N 21/35
[52] U.S. Cl. .................. 250/339.12; 250/339.11
[58] Field of Search .......................... 250/339.12, 339.11

[56] References Cited

U.S. PATENT DOCUMENTS 4,800,279   1/1989   Hieftje et al. .................. 250/339.12

FOREIGN PATENT DOCUMENTS

WO96/24843   8/1996   WIPO.

OTHER PUBLICATIONS

Animal Feed Sci. & Tech., vol. 37, No. 3–4, 1992, "Influence of growth type and season . . . ", Givens et al, pp. 281–295.

Animal Feed Sci. & Tech., vol. 51, Feb. 1995, "The use of NIRS to predict the chemical . . . ", de Boeuer et al, pp. 243–253.

Proceedings 9$^{th}$ Eur. Poul. Conf., U.K., Aug. 7–12, vol. 2, "Current status of near infrared . . . ", Flinn et al, pp. 106–109.

Agri–Practice, vol. 12, No. 3, May/Jun. 1991, "Forage Analyses for Dietary Diagnosis . . . ", Anderson et al, pp. 29–32.

Bulgarian Journal of Agri. Sci., vol. 1, 1995, "Estimation of Composition, Digestibility . . . ", Atanassova et al, pp. 35–44.

Derwent Abstract Accession No. 93–180660/22, SU 1739284 A1, Jun. 7, 1992.

Proceedings of the XVII Int'l. Grassland Congress, 1993, "Genotypes of dry matured . . . ", Baker et al, pp. 592–593.

Proceedings of the XVII Int'l. Grassland Congress, 1993, "Compositions of the fractions . . . ", Klein et al, pp. 593–595.

Patent Abstracts of Japan, p. 1060, JP 53–15890 (Shimazu Seisakusho K.K.), Feb. 14, 1978.

Patent Abstracts of Japan, JP 06–123700 (Hamamatsu Photonics KK) May 6, 1994.

Patent Abstracts of Japan, p. 58, JP 60–98335 (Kogyo Gijutsuin), Jun. 1, 1985.

*Primary Examiner*—Constantine Hannaher
*Assistant Examiner*—Otilia Gabor
*Attorney, Agent, or Firm*—Jacobson, Price, Holman & Stern, PLLC

[57] ABSTRACT

A method for determining a biomechanical property of a feed using infrared radiation to obtain spectral data on the feed. The spectral data is used to determine the biomechanical property based on the bond energies of the chemical constituents of the feed.

28 Claims, 11 Drawing Sheets

Digestibility of dry matter in vitro (%)

Stepwise 2,5,5

Energy required to compress (kJ/kg DM)

Stepwise 2,10,10

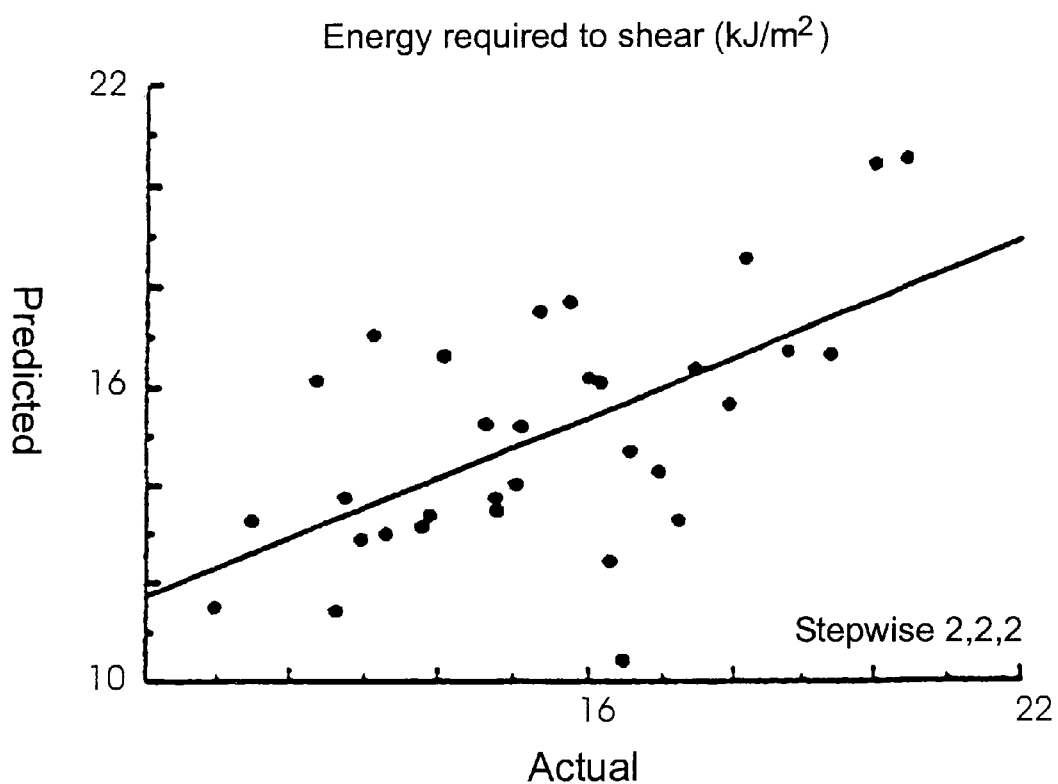

Digestibility of dry matter in vivo (%)

Step-up 2,10,5, (3 terms)

Energy required to compress (kJ/kg DM)

Step-up 2,10,5 (3 terms)

Digestibility of dry matter in vitro (%)

Step-up 2,10,10 (4 terms)

Energy required to shear (kJ/m²)

Step-up 2,5,5

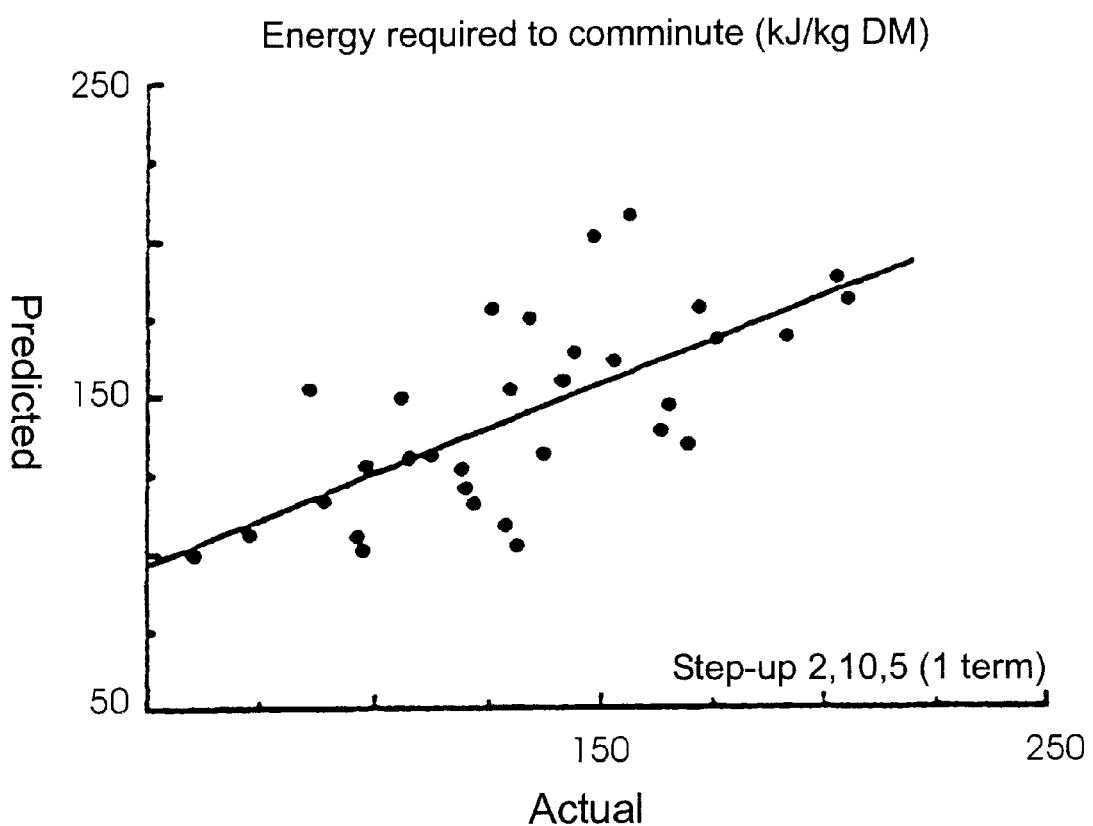

Digestibility of dry matter in vitro (%)

Energy required to compress (kJ/kg DM)

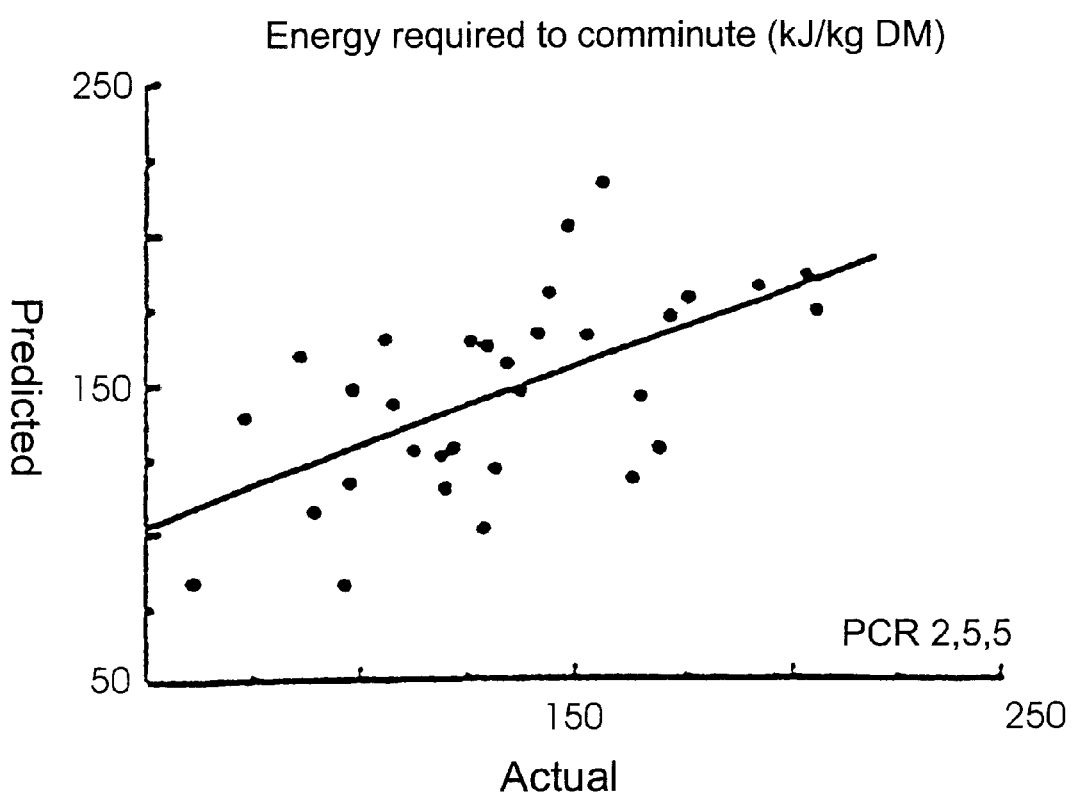

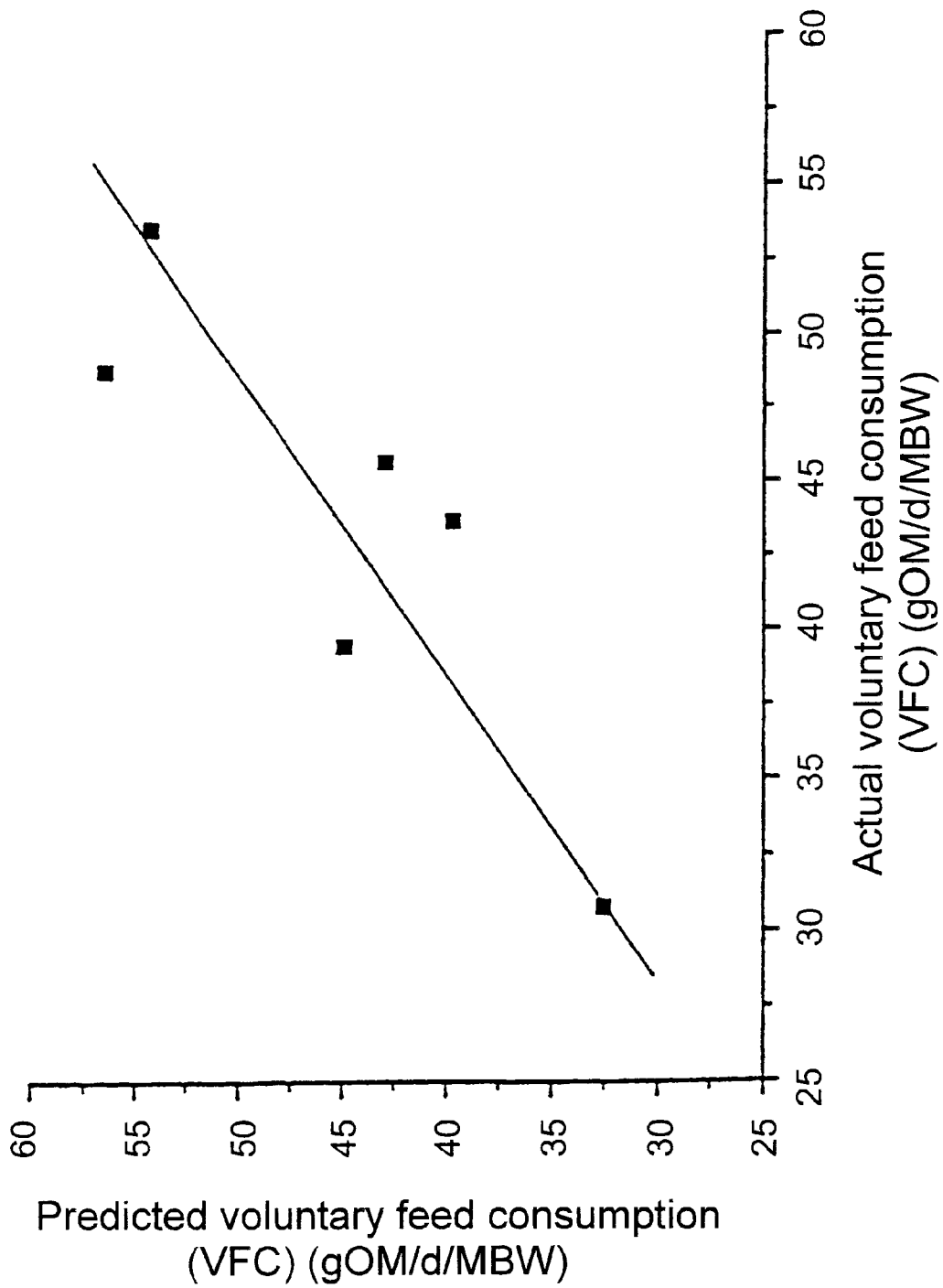

METHOD FOR DETERMINING FEED QUALITY

This invention relates to a method for quantifying biomechanical properties of animal feed based on a correlation between the chemical and biomechanical properties of the feed, and to methods for objectively measuring the quality of animal feed, such as fodders including hay, pastures and forages.

Diet is the major determinant of productivity of an animal. In the livestock industry, animals are farmed for meat, wool and other valuable products. The diet of farmed livestock is largely dictated by man and, given the effect of diet on animal production it is highly desirable to optimize the diet of livestock to gain maximum benefit from the natural resource.

Feed quality is one variable that has a major impact on animal productivity. In this respect, feed quality affects the amount of feed an animal will consume and the feeding value it gains from the feed consumed. In the case of cattle, sheep and other ruminants, feed quality depends on digestibility, chemical attributes (nutrient composition) and biomechanical attributes (namely how easy it is for an animal to chew the feed during ingestion and rumination).

It is generally accepted that there are constraints on the intake of feed by ruminant animals, that the amount of useful energy obtained by a ruminant animal may fail short of the amount that the animal can potentially use, and that this would result in reduced productivity. For example, the principal constraints to voluntary intake of fodders are resistance of fodder fibre to chewing and digestibility (provided that the intake is not otherwise constrained by low palatability, deleterious secondary compounds, or the inadequacy of essential nutrients). Differences between feeds, such as fodders, in their resistance to chewing are reflected in differences in biomechanical properties, including comminution energy, shear energy, compression energy, tensile strength, shear strength and intrinsic shear strength.

Hay is a common feed and its quality is significantly affected by factors such as seasonal differences, haymaking practices and pasture composition. It has been shown in one recent survey that in some years as little as 11% of hay produced was good enough to promote liveweight gain in weaner sheep. This possibility of wide variation in measures of hay quality is a matter of increasing concern, and has given rise to a demand for a method of objective quality assessment.

A hay quality system adopted in the United States of America uses a measure known as relative feed value (RFV) to distinguish between hays of different quality. The RFV is calculated from the dry matter digestibility, which is predicted from acid detergent fibre (ADF) content, and from the dry matter intake, which is predicted from neutral detergent fibre (NDF) content.

The RFV based system suffers from a number of disadvantages. For example, the ADF and NDF contents of fodders are determined by chemical methods which take several days to complete, and thus are expensive in terms of resources.

While objective quality assessment and product specification has become an integral part of the production and marketing in domestic and export markets for the Australian grain, wool, meat and dairy industries, performance-based quality standards are not presently in place for feeds such as hays and other fodders. Consequently;

(a) the feed buyer cannot be sure of getting value for money, and this is likely to become increasingly important in respect of export markets if other exporting countries are able to guarantee standards for their product;

(b) the feed producer cannot be sure of getting a higher price for a superior product;

(c) livestock producers are unable to objectively formulate rations or supplementary feeding regimes to achieve animal production targets; and (d) the market for animal feed tends to be unstable.

Whilst the relationship between biomechanical properties of feed and feed quality is now accepted, there is a need for a convenient, inexpensive and relatively accurate assay method for feed to determine its quality. An accurate determination of feed quality allows for optimisation of feeding regimes and improved animal production for obvious economic gains.

It is an object of this invention to overcome or at least partially alleviate the aforementioned problems and/or reduce the uncertainties and concomitant problems of the prior art systems for measuring the biomechanical properties of feed and hence determining feed quality.

Thus, the present invention provides a method for determining a biomechanical property of a feed, the method comprising the steps of;

(a) subjecting the feed to infrared radiation to obtain spectral data: and (b) using the spectral data to determine the biomechanical property;

whereby the biomechanical property of the feed is determined on the basis of the bond energies of the chemical constituents of the feed.

The spectral data may be used directly to determine the biomechanical property of the feed. Alternatively, the spectral data may be used to determine another property of the feed and the other property is used to determine the biomechanical property on the basis of a correlation between the other property and the biomechanical property.

When the biomechanical property is determined via another property, the other property is preferably a chemical property of the feed such as the ADF content or the NDF content or the lignin content.

There is a variety of biomechanical properties of the feed that may be determined. Preferably, the biomechanical properties are selected from the group comprising shear energy, compression energy, comminution energy, tensile strength, shear strength and intrinsic shear strength.

The spectral data may comprise a reflectance spectrum at a combination of wavelengths or over a predetermined range of wavelengths such as 700 nm–3000 nm, or more preferably 1100 nm–2500 nm. Preferably, the data obtained for the spectral range of 1850 nm–1970 nm is disregarded, this being the range over which water reflects strongly.

The spectral data may be recorded at one or more wavelength intervals throughout the spectral range. When the spectral data is a reflectance spectrum over a predetermined range it is preferably measured at 2 nm intervals over the range. Of course, if so desired the spectral data may be measured at intervals other than 2 nm.

When the spectral data is used to directly determine a biomechanical property, the biomechanical property is preferably determined by comparison of the spectral data with a calibration equation that reflects the relationship between reflectance and the biomechanical property. Preferably, the calibration curve is determined on the basis of laboratory data establishing a correlation between reflectance and the biomechanical property.

Thus, the present invention also provides a method for determining a biomechanical property of a feed, the method comprising the steps of;

(a) subjecting the feed to infrared radiation to obtain spectral data; and (b) comparing the spectral data obtained in (a) with a calibration equation to determine the biomechanical property;

whereby the biomechanical property of the feed is determined on the basis of the bond energies of the chemical constituents of the feed.

The present invention also provides a method for determining feed quality, the method comprising the steps of;

(a) subjecting the feed to infrared radiation to obtain spectral data;

(b) using the spectral data to determine a biomechanical property of the feed; and (c) using the value of the biomechanical property obtained in step (b) to determine feed quality;

whereby the biomechanical property of the feed and thus the feed quality is determined on the basis of the bond energies of the chemical constituents of the feed.

In one particular form, the method described immediately above may further comprise the determination of an additional property of the feed. The additional property may vary and preferably is selected from the group comprising the digestibility of the feed in vivo or in vitro, the ADF content or the NDF content, or the lignin content.

The present invention is based on research establishing a strong correlation between the bond energies as they relate to the physical structure, and the biomechanical properties of feed. Once this correlation is established the bond energies of the chemical constituents, and in turn the biomechanical properties of the feed, can be determined using infrared spectroscopy. The biomechanical properties quantified in this way are useful for accurately determining feed quality.

In this respect, research resulting in the present invention has shown that the biomechanical attributes of feeds such as cereal and legume hays, straws, and mature, dry subterranean clovers are much more strongly related to animal performance than are digestibility or chemical composition of the feeds.

Thus, comminution energy, the energy required to grind or comminute fodder material, has proved to be a very effective indicator of forage consumption constraint (FCC), which is the difference between the quantity of forage an animal should consume to satisfy its capacity to use energy (a theoretical maximum) and the actual voluntary dry matter intake achieved.

Shear energy, the energy required to shear fodder material, and compression energy, the energy required to compress fodder material, are two biomechanical feed characters of fodders that are closely related to comminution energy and which also are good predictors of FCC.

In this respect, feed quality can be assessed in a number of ways. The forage consumption constraint (FCC) is one convenient measure of feed quality and equates to the difference between the quantity of the fodder that the animal would be attempting to consume to satisfy its capacity to use energy (theoretical maximum intake) and the voluntary forage consumption (VFC).

Thus, the present invention also provides a method for determining feed quality, the method comprising the steps of:

(a) subjecting the feed to infrared radiation to obtain spectral data;

(b) using the spectral data to determine a biomechanical property of the feed, and (c) using the value of the biomechanical property obtained in step (b) to determine the forage consumption constraint (FCC) or voluntary feed consumption (VFC) as a measure of feed quality;

whereby the biomechanical property of the feed and thus the feed quality is determined on the basis of the bond energies of the chemical constituents of the feed.

The present invention is based on the finding that variations in biomechanical properties such as shear energy, comminution energy and compression energy are reflected in NIR spectra of fodders. This finding, together with recognition of the value of biomechanical characters for the prediction of FCC (and, in turn, the prediction of voluntary feed consumption (VFC)) makes it possible for quicker, less expensive, more convenient and more reliable prediction of feed quality than hitherto known and predicted.

Accordingly, this invention provides a method of (i) assessing the suitability of a fodder, such as a forage, to meet a required animal performance; or (ii) predicting the VFC of a forage; or (iii) predicting the FCC of a forage, which method comprises subjecting a sample of the forage to NIR radiation and determining the reflectance at selected wavelengths.

It has been found that the biomechanical properties, such as shear and comminution energy values for a given fodder, correlate with the fodder's reflectance of infrared radiation. More specifically, the invention is based on research showing that:

(a) NIR wavelengths at which reflectance (R), namely the second derivative of the logarithm of the inverse of R, correlates significantly with the variation in energy required to shear fodder materials are 1168 nm, 1458 nm, 1598 nm, 1718 nm, 1828 nm and 2048 nm. For the prediction of fodder shear energy ($y_1$, $kJ.m^{-2}$) the following equation may be used:

$$y_1 = 19.95 + 10239.46 R_{1168} + 3623.49 R_{1458} - 4255.61 R_{1598} - 5319.88 R_{1718} + 5148.38 R_{1826} + 2452.05 R_{2048}$$

(b) NIR wavelengths at which the second derivative of the logarithm of the inverse of reflectance (R) correlates significantly with the variation in energy required to comminute fodder materials are 1138 nm, 2018 nm, 2128 nm and 2408 nm.

For the prediction of fodder comminute energy ($y_2$, $kJ.kg\,DM^{-1}$) the following equation is proposed:

$$y_2 = 231.42 + 18224.74 R_{1138} - 4955.12 R_{2018} - 3005.37 R_{2128} + 4290.18 R_{2408}$$

(c) NIR wavelengths at which the second derivative of the logarithm of the inverse of reflectance (R) correlates significantly with the variation in compression energy are 1268 nm, 1588 nm, 1728 nm, 2278 nm. For the prediction of compression energy ($y_3$, $kJ.kgDM^{-1}$) the following equation may be used:

$$y_3 = -0.71 - 911.04 R_{1268} + 112.57 R_{1558} - 79.48 R_{1728} - 28.02 R_{2278}$$

(d) NIR wavelengths at which the second derivative of the logarithm of the inverse of reflectance (R) correlates significantly with variation in in vivo digestibility of dry matter (DMD) ($y_4$, %) is 1158 nm, 1238 nm, 1668 nm, 1908 nm, 1918 nm, and 2248 nm. For prediction of the DMD ($y_4$, %) of a fodder the following equation is proposed:

$$y_4 = 46.62 + 8162.72R_{1158} - 8799.69R_{1238} + 1249.01R_{1668} + 519.46R_{1908} - 367.08R_{1918} - 161.84R_{2248}$$

(e) NIR wavelength at which the second derivative of the logarithm of the inverse of reflectance (R) correlates significantly with variation in in vitro digestibility of dry matter (IVDMD) is 1698 nm, 1748 nm, 1908 nm, 1918 nm and 2158 nm. For prediction of the DMD (in vitro) of a fodder the following equation is proposed:

$$y_5 = 63.43 - 2186.89R_{1698} - 1491.99R_{1748} + 981.30R_{1908} - 556.01R_{1918} + 2003.05R_{2158}$$

Accordingly, in a preferred method according to this invention, the infrared wavelengths at which reflectance is measured comprise one or more of the following: 1168 nm, 1458 nm, 1598 nm, 1718 nm, 1828 nm, 2048 nm, 1138 nm, 2018 nm, 2128 nm, 2408 nm, 1268 nm, 1588 nm, 1728 nm, 2278 nm, 1158 nm, 1238 nm, 1668 nm, 1908 nm, 2248 nm, 1698 nm, 1748 nm, 1918 nm and 2158 nm.

It will be understood that the foregoing are wavelengths at which the strongest correlations have been observed, and the possibility of useful correlations being observed at other wavelengths are highly likely.

Essentially, it can be shown that in the same way that a decrease in comminution energy is reflected by a decrease in forage consumption constraint, there is also a linear relationship between comminution energy or shear energy and the consumption constraint of a fodder. Thus, the use of NIR spectra, in conjunction with the equations detailed at paragraphs (a) to (e) above, permits estimation of the VFC of a fodder, which together with estimates of digestibility (conveniently obtained from NIR spectra) can be expected to provide a valuable basis for performance-based quality standards for fodders.

It is to be appreciated that the intention of this invention is to offer a quick, reliable and relatively inexpensive means of obtaining information from which the fodder producer and user, such as purchaser, might make informed judgements about the market value of a given fodder sample relative to alternatives, and of its suitability for a particular purpose.

Conceivably, fodder quality predictions obtained by the method of this invention could be a useful component of, or used in conjunction with, for example, Decision Support Software (DSS) packages designed to assist livestock management.

It is further envisaged that by combining NIR measurements made by a remote sensing system, such as Landsat, with data from a Geographical Information System, the invention will provide a means of making reliable predictions of pasture quality. These predictions, together with predictions of feed intake and animal performance, should then provide a useful basis for strategies of supplementary feeding to improve performance in grazing ruminants.

The present invention also provides for a spectrometer configured to determine biomechanical properties and/or quality of feed according to the methods of the present invention. Preferably, the spectrometer includes a data processing means which enables the spectrometer to receive a feed sample and quantify either or both the biomechanical properties of the feed and the quality of the feed. In one particular form the data processing means includes a calibration equation to facilitate the determination of the feed quality or biomechanical property.

BRIEF DESCRIPTION OF THE DRAWINGS

FIGS. 2a–2e are graphs illustrating simple linear correlation coefficient between laboratory determined and NIR predicted values for each of the biomechanical characters and digestibility of dry matter of a sample in the validation set.

FIGS. 3a–3e are graphs illustrating simple linear correlation coefficient between laboratory determined and NIR predicted values for each of the biomechanical characters and digestibility of dry matter of a sample in the validation set.

FIGS. 4a–4e are graphs illustrating simple linear correlation coefficient between laboratory determined and NIR predicted values for each of the biomechanical characters and digestibility of dry matter of a sample in the validation set.

FIG. 5 is a graph of predicted voluntary feed consumption versus actual voluntary feed consumption.

Figure 1:
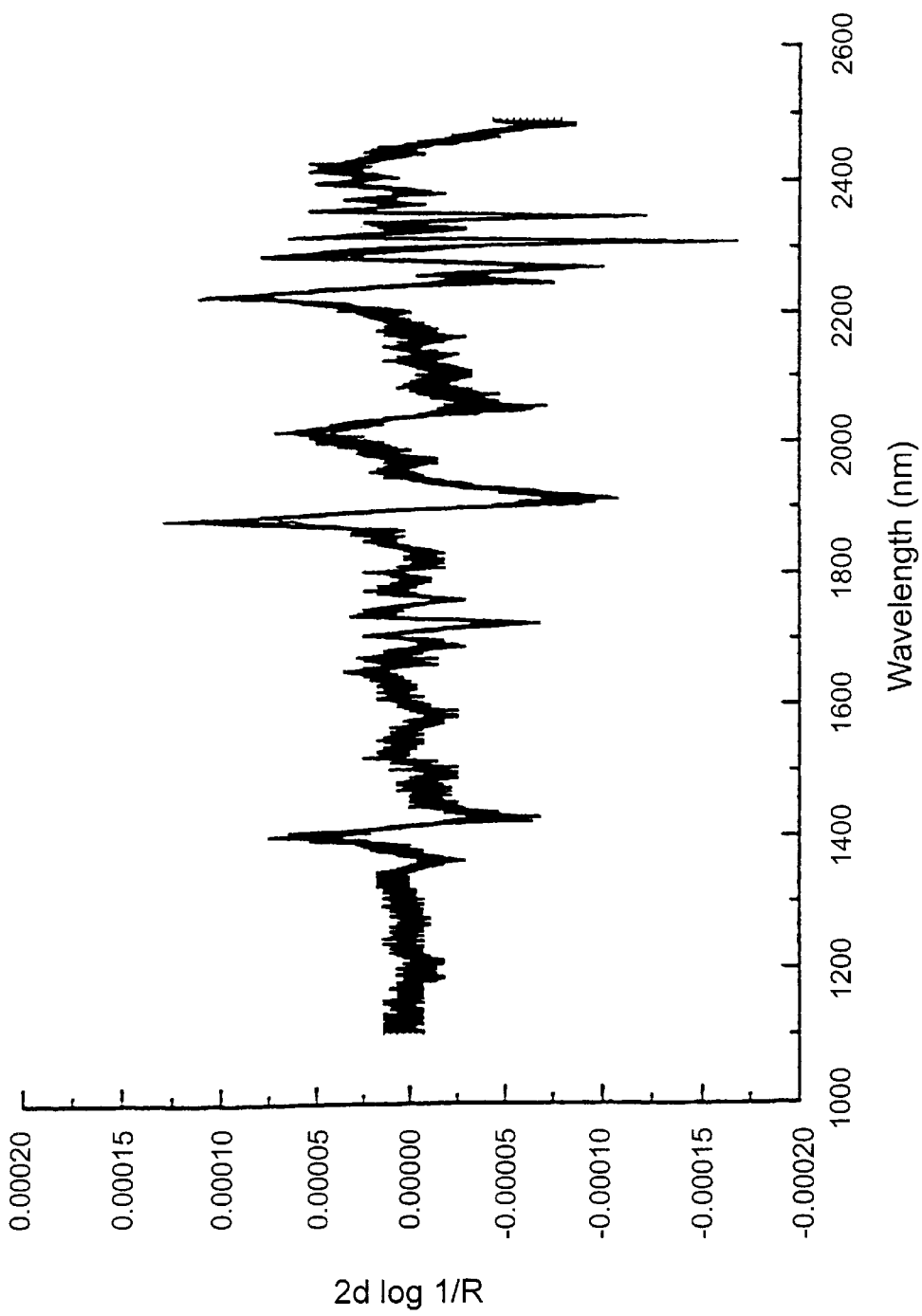
FIG. 1 is a graph of spectra of samples in the validation and calibration sets.
Figure 2A:
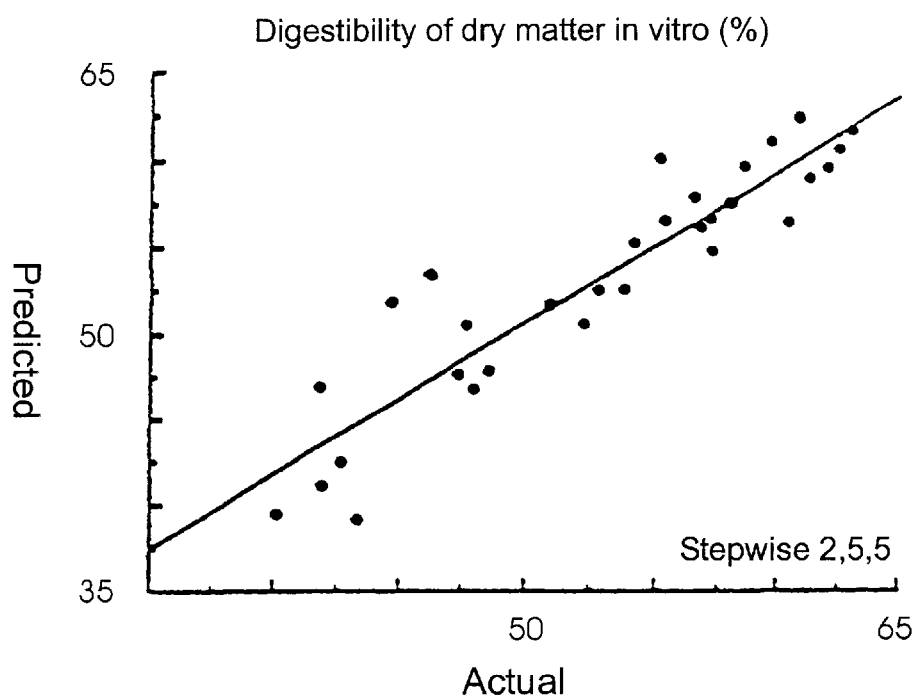
Figure 2B:
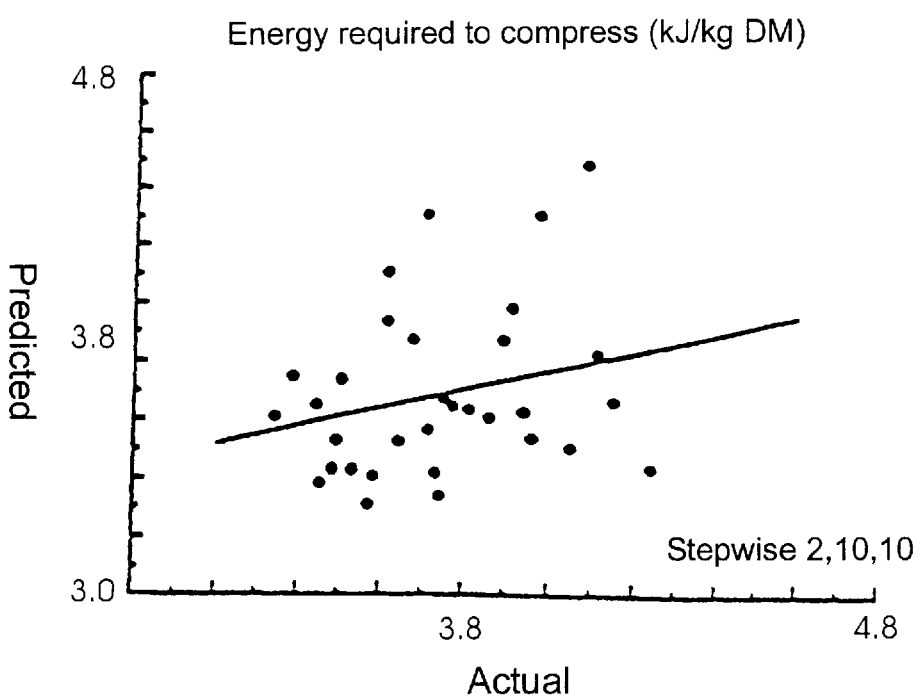
Figure 2C:
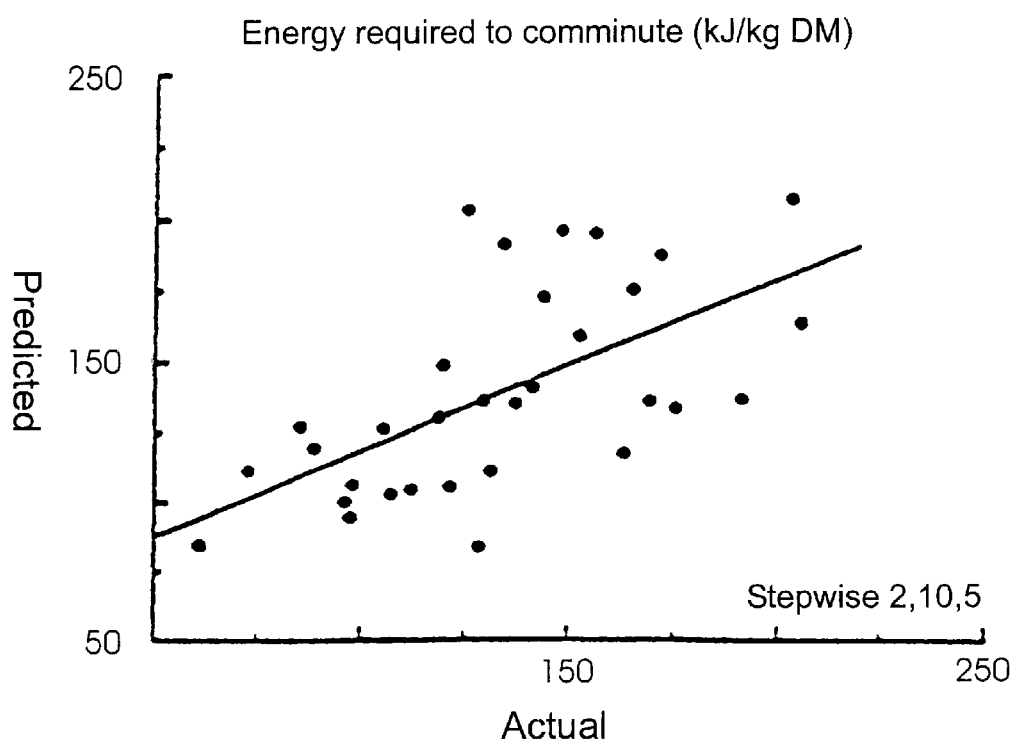
Figure 2D:
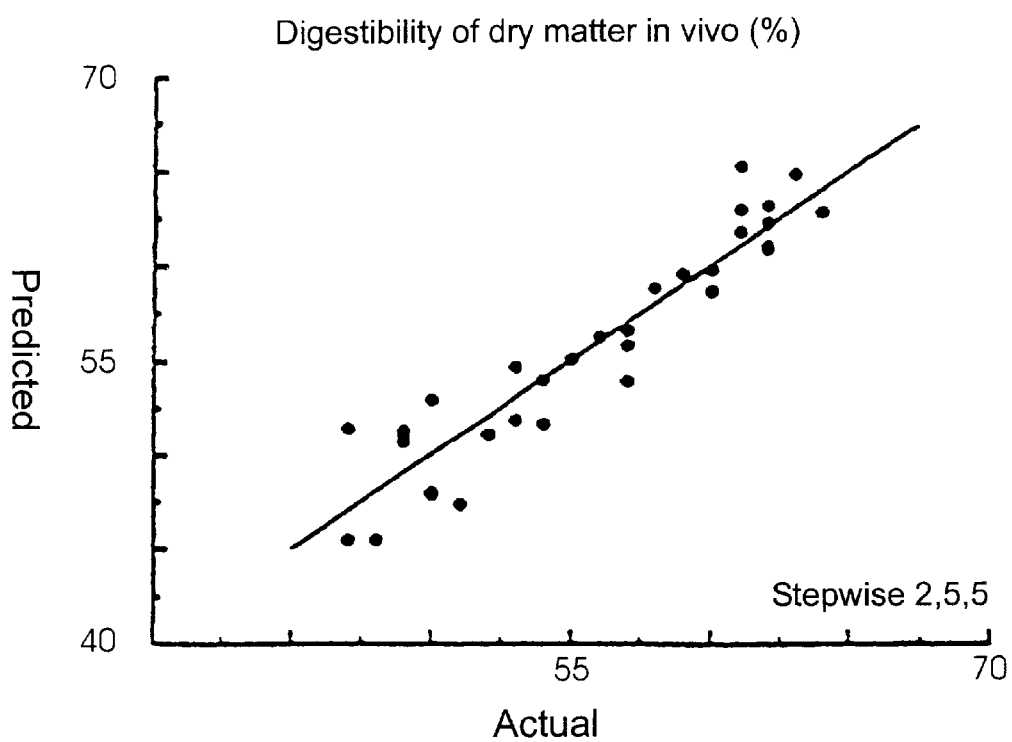
Figure 3A:
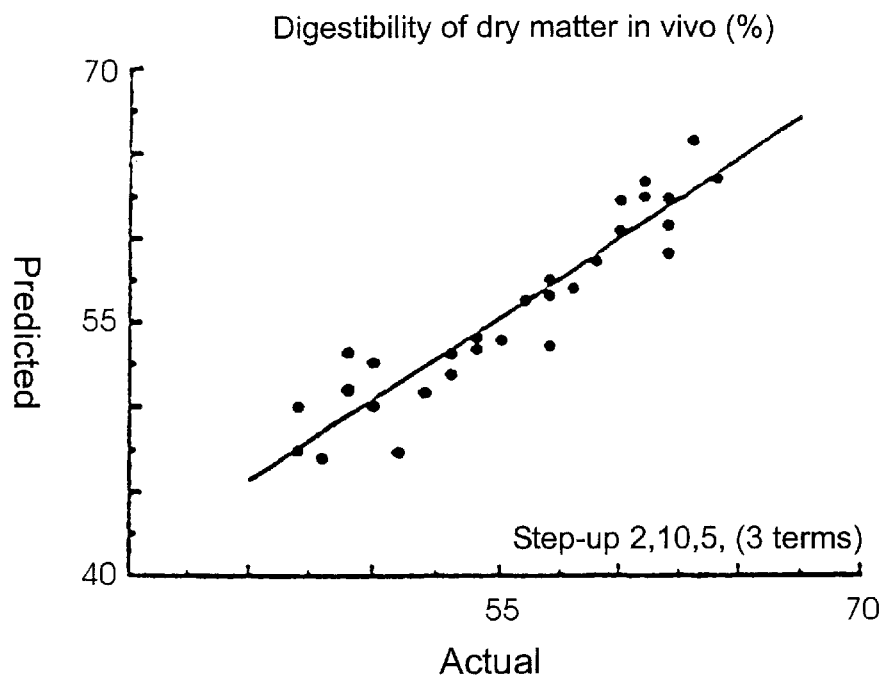
Figure 3B:
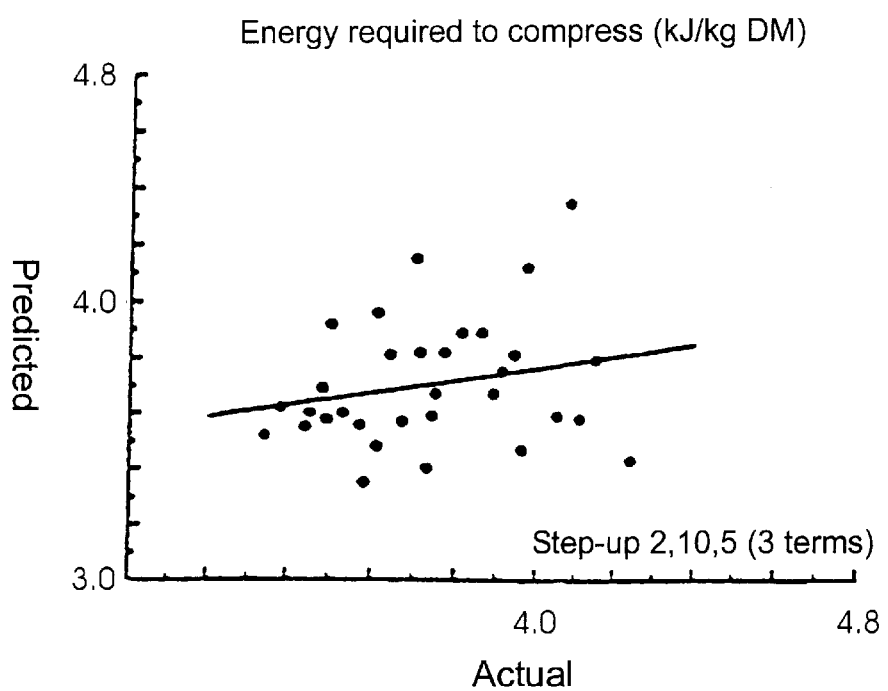
Figure 3C:
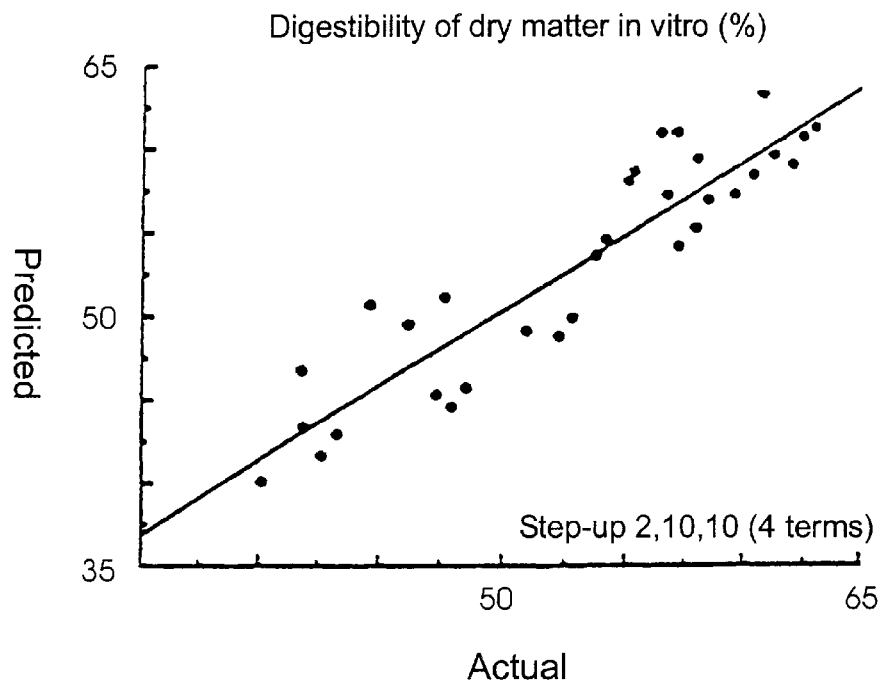
Figure 3D:
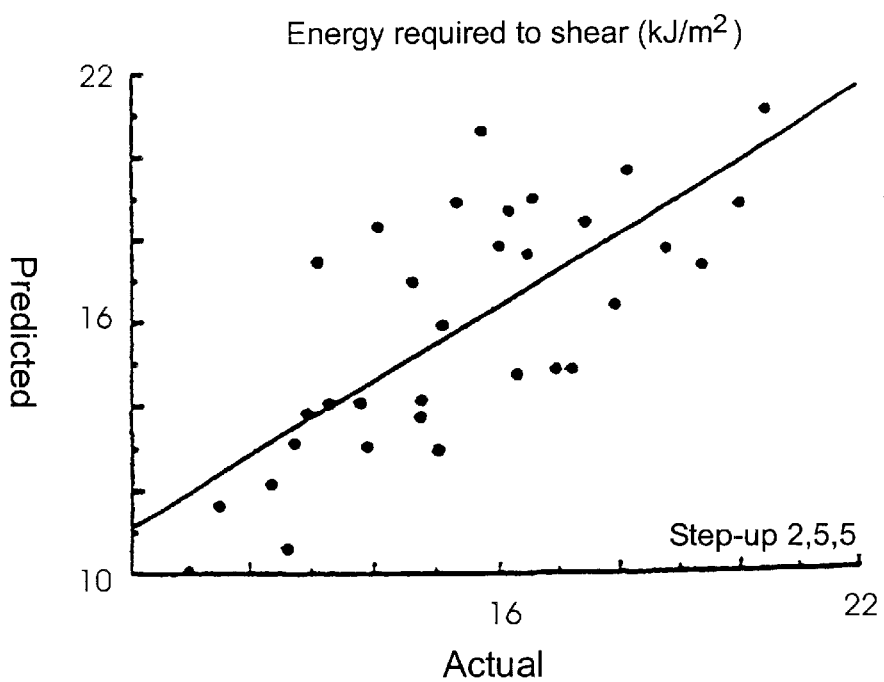
Figure 4A:
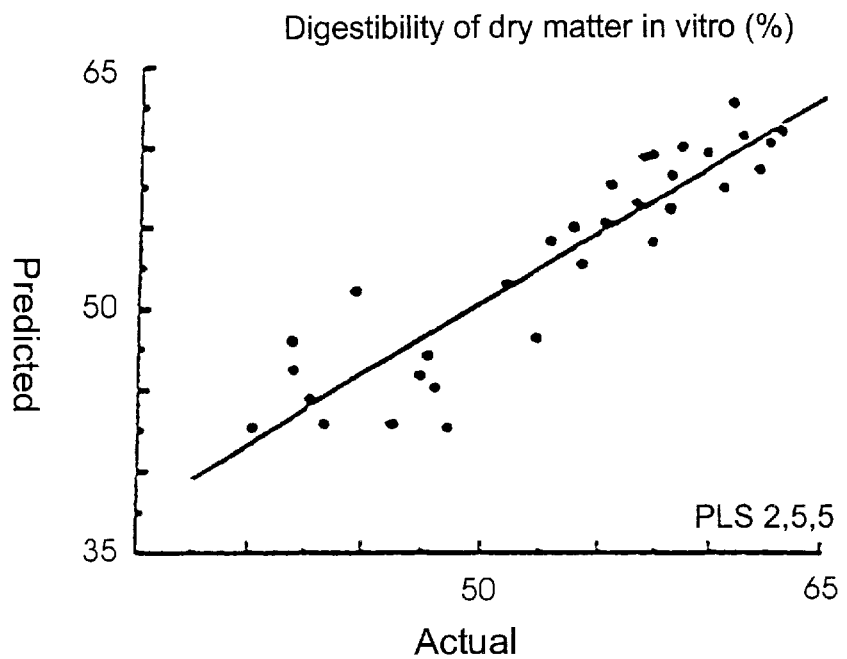
Figure 4B:
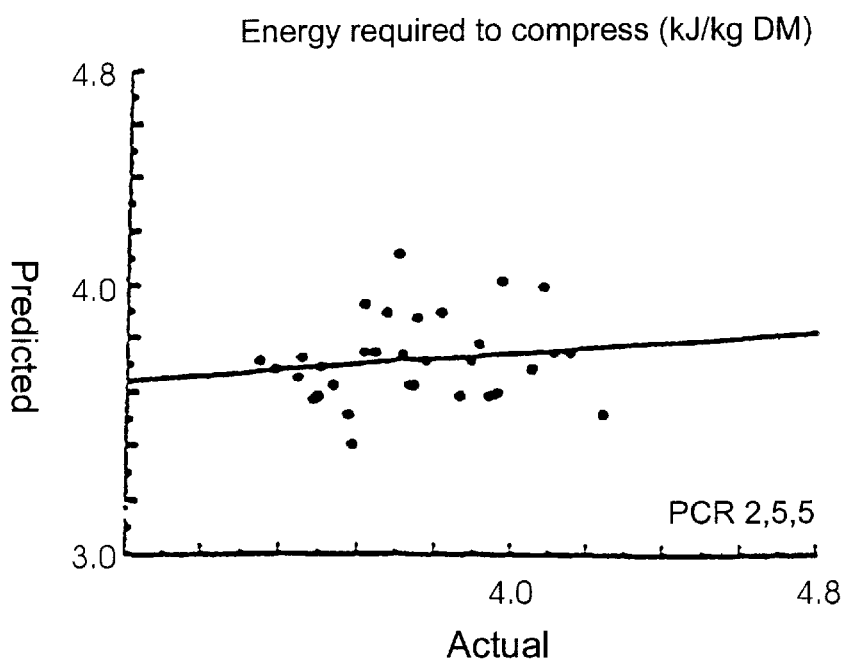
Figure 4C:
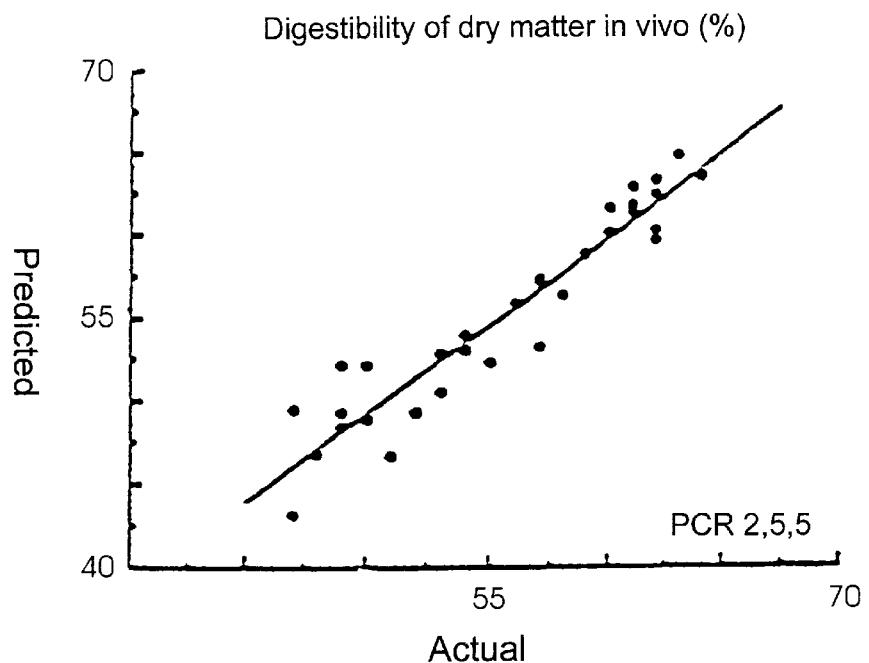
Figure 4D:
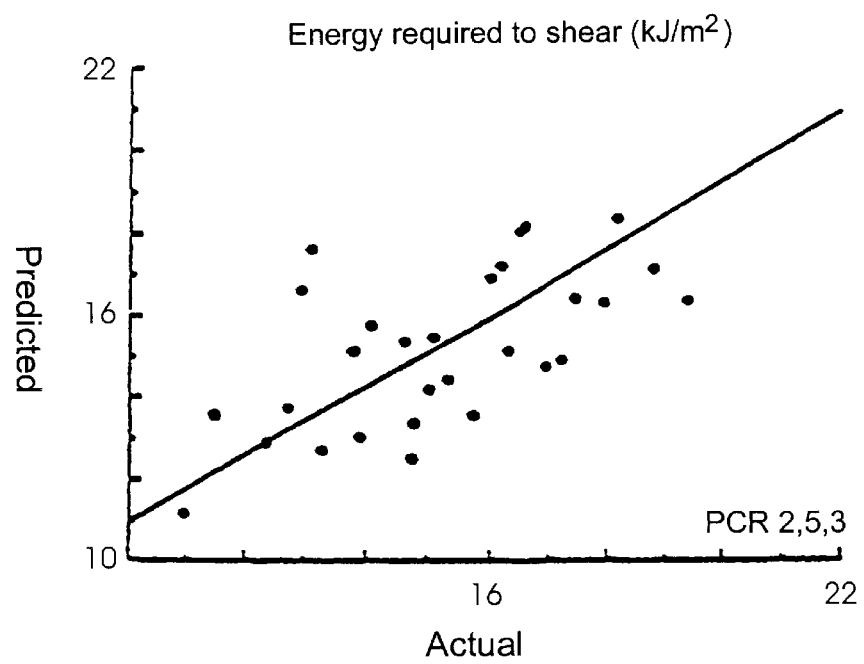

The invention will now be described with reference to the following examples. The description of the examples is in no way to limit the generality of the preceding paragraphs.

EXAMPLES

The energy of molecular vibrations correspond to the energy of the infrared spectrum of the electromagnetic spectrum, and these molecular vibrations may be detected and measured in the wavelength range of the infrared spectrum. Functional groups in molecules have vibration frequencies that are characteristic of that functional group and that are within well-defined regions of the infrared spectrum.

For organic compounds the principal analytical features of the near infrared (NIR) spectrum are due to absorbance of radiant energy by bonds between hydrogen, carbon, nitrogen, oxygen or with sulphur, phosphorus and metal halides. When organic compounds are irradiated with infrared radiation at wavelengths between 700 and 3000 nm part of the incident radiation is absorbed and the remainder is reflected, refracted or transmitted by the sample. Most quantitative reflectance analyses are made in the wavelength range of 1100 to 2600 nm. The amount of energy absorbed or diffusely reflected at any given wavelength in this wavelength range is related to the chemical composition of the organic compound. NIR spectroscopy uses detectors to measure the amount of radiation that is diffusely reflected by the irradiated sample.

NIR spectroscopic analysis is an analytical procedure calibrated to a primary reference method. Calibration in NIR spectroscopy (NIRS) relies on similarities among the spectra, and analytical properties of interest in the reference samples. In this example the analytical properties of interest were the biomechanical characters of forages, and the procedure that was adopted in this example was as follows:

a) prediction of biomechanical characters of a range of grasses using NIR spectroscopy was established by developing a calibration equation(s) from laboratory determined values of a set of reference samples.

b) validation of the equation(s) either by using laboratory determined values of a separate set of samples, or by a cross-validation procedure using the laboratory determined values of the reference samples.

c) using the NIRS-predicted values for biomechanical characters of the forages and for digestibility of the forages, forage consumption constraint (FCC) was predicted, and in turn voluntary feed consumption (VFC) was predicted.

d) the predicted FCC and VFC were compared with actual data from groups of animals fed each of these forages.

Example A

Developing a Calibration Equation to Predict Biomechanical Properties of Herbage The samples used in this example were a range of varieties of Panicum spp. harvested at a range of plant maturities throughout the growing season (Table 1). Each of the samples was dried and chaffed, and then fed to groups of sheep (8 sheep per group) which were penned individually, to determine in vivo dry matter digestibility (DMD), VFC and FCC. Samples of the hays were stored for laboratory analyses.

Biomechanical properties of the forages were determined using published methods; the energies required to shear or compress the forages according to Baker, Klein, de Boer and Purser (Genotypes of dry, mature subterranean clover differ in shear energy. Proceedings of the XVII International Grassland Congress 1993. pp 592–593.) and the energy required to comminute the forages according to Weston, R. H. and Davis, P (1991) 'The significance of four forage characters as constraints to voluntary intake' p.33 in 'Proceedings of The Third International Symposium on the Nutrition of Herbivores' (Compiled by: Wan Zahari, M., Amad Tajuddin, Z., Abdullah, N. and Wong, H. K. 'Published by the Malaysian Society of Animal Production (MSAP). ISBN: 967-960-026-2). In vitro digestibility of dry matter (IVDMD) was determined by the pepsin-cellulase technique as modified by Klein and Baker (Composition of the fractions of dry, mature subterranean clover digested in vivo and in vitro. Proceedings of the XVII International Grassland Congress 1993. pp593–595.).

There are several ways to process samples for NIRS analysis, and in this example the samples were ground through a cyclone mill with a 1 mm screen and equilibrated at 25° C. or at least 24h before NIRS analysis. The samples were scanned by monochomating near infrared reflectance spectrophotometer (Perstorp NIRS 6500) and the absorption spectra recorded for the range 1100 to 2500 nm at 2 nm intervals. One spectral range 1850 to 1970 nm, where water absorbs strongly, was disregarded in further analysis of the spectral data.

For NIRS analysis the samples were divided into two groups: one group to be used as a 'calibration' set to establish a prediction equation, and a second group, the 'validation' set, to be used to validate the prediction equation. There are a number of ways to select the samples for each set. In this example the samples were ranked according to each of the characters that were to be predicted and every other sample was selected for the calibration set (33 samples) and the validation set (32 samples). Thus, for each character that was evaluated, a different selection was made from the 65 samples to establish the respective calibration and validation sample sets.

The ranges, mean, median and variation in the laboratory-determined values for each of the characters of interest in the calibration and validation sets are listed in Table 2.

The software for scanning, mathematical processing and statistical analysis were supplied with the spectrophotometer by the manufacturers. The spectral data were transformed by taking the second derivative of the logarithm of the inverse of the reflectance (R) at each wavelength (d" log (1/R)). The similarities amongst the spectra (FIG. 1) of the samples in the validation and calibration sets were determined using principal components scores to rank the spectra according to the Mahalanobis distance from the average of the spectra. The Mahalanobis distance values were standardized by dividing them by their average value, and were denoted 'global' H values (Table 3).

Calibration equations were developed using the calibration samples by regressing the data from the laboratory analyses of each biomechanical property against the corresponding transformed spectral data using the following mathematical methods:

a) Stepwise linear regression
b) Step-up linear regression
c) Principal components regression (PCR)
a) Partial least squares regression (PLS). and
e) Modified partial least squares regression (MPLS).

Stepwise calibrations were developed for each calibration set of samples using the mathematical treatments of the spectral data 2,2,2; 2,5,5; 2,10,5; and 2,10,10; where the first number denotes that the second derivative was used, the second indicates that second derivatives of the spectral data (determined at 2 nm intervals) were taken at intervals of 4, 10 or 20 nm, and the third indicates that the function was smoothed using the 'boxcar' method over intervals of wavelength of 4, 10, or 20 nm (Table 4a). Likewise step-up calibrations were developed for each calibration set with up to 6 terms in each calibration equation using mathematical treatments 2,2,2; 2,5,5; 2,10,5; and 2,10,10 (Table 4b). Calibrations developed for each calibration set using principal components regression, partial least squares regression, or modified partial least squares regression each were developed using mathematical treatments 2,5,5 and 2,10,10 (Table 4c).

In developing the calibration equations in the stepwise and step-up regressions, only wavelengths with partial F-statistic of more than 8 were accepted for the models.

For each calibration using each calibration set the following calibration statistics were determined:

a) Squared multiple correlation coefficient ($R^2$), an indication of the proportion of the variation in the calibration set that is adequately modelled by the calibration equation.
b) The standard error of calibration (SEC) together with its confidence interval (±CL), which is the standard deviation for the residuals due to difference between the laboratory determined (reference) and the NIR predicted values for samples within the calibration set Once the calibration equations were developed, each equation was validated by using it to predict the respective biomechanical property values for each sample in the validation sample set. For each calibration equation the following validation statistics were determined:

a) Simple linear correlation coefficient ($r^2$) between the laboratory determined and NIR predicted values.
b) The bias (or systematic error) in the regression relationship between the laboratory determined (reference) and NIR predicted values.
c) The confidence limits of the bias in the regression relationship between the laboratory determined (reference) and NIR predicted values.
d) The standard error of prediction, corrected for bias (SEP(C)), which represents the unexplained error of the prediction, the deviation of the differences between laboratory determined and NIR predicted values.
e) The coefficient of determination, or slope ($\beta$), and y-intercept ($\alpha$) of the linear regression relationship between the laboratory determined and NIR predicted values.

f) The residual standard deviation (RSD) of the linear regression relationship between the laboratory determined and NIR predicted values.

In addition, the calibration equations were validated using a procedures of cross-validation. These are procedures where every sample in the calibration set was used once for prediction, and the standard error of validation corrected for bias (SEV(C), for stepwise and step-up regressions) and cross-validation (SECV, for multivariate regressions) can be determined.

Calibration equations for each biomechanical character were selected using the following criteria:

a) Lowest partial F-ratio, highest $R^2$, lowest SEC and, for PCR, PLS and MPLS, lowest SEV(C) (or, for multivariate regressions, SECV)

b) Highest $r^2$, lowest bias and |bias|<bias confidence limit. lowest SEP(C), β closest to 1.0, α closest to 0, and lowest RSD. As well, SEP(C) was compared with the standard error of laboratory determined values amongst all 65 samples, listed in Table 5.

Calibration equations were similarly established to predict in vivo digestibility and in vitro digestibility. The coefficients for each wavelength in the selected calibration equations from stepwise or step-up regression analyses are listed in Table 6a, and those from multivariate analyses are listed in Table 6b.

Simple linear correlation coefficient ($r^2$) between the laboratory determined and NIR predicted values for each of the biomechanical characters (energies required to shear, comminute or compress) and digestibility of dry matter determined in vivo or in vitro of the samples in the validation set are shown in FIGS. 2a–2e, 3a–3e, and 4a–4e. NIR predicted values are predicted using calibration equations that best met the criteria listed above.

Example B
Prediction of FCC and VFC Using NIR Determinations of Energy Required to Shear and In Vivo Digestibility To demonstrate the prediction of voluntary feed consumption using NIR determined values for a biomechanical character and digestibility of forages, samples of Panicum spp. hay were selected which were common to both of the validation sample sets used to establish the NIR prediction equations for energy required to shear and in viva digestibility. The hays represented the range of varieties in the sample set, and are listed in Table 7. The samples were scanned by the same spectrophotometer that was used to establish the calibration equations, and the absorption spectra were recorded in the range 1100 to 2500 nm at 2 nm intervals. Values for energy required to shear and in vivo digestibility were predicted from calibration equations (Tables 4a 4b and 4c) using the recorded spectra data.

These values then were used to estimate FCC from the relationship between biomechanical character(s) and FCC of the range of forages used by Weston and Davis (1991). Energy required to shear the forages used by Weston and Davis was determined according to Baker et al. (1993). The relationship between the energy required to shear these forages ($kJ/m^2$) and FCC (g organic matter (OM)/d/kg metabolic body weight (MBW)) was described by the relationship:

$$\text{Energy required to shear } (x) = -26.13 + 5.53(\text{FCC}(y))$$

where R=0.92; RSD=8.70; N=13; P<0.0001.

FCC from this relationship and in vivo digestibility predicted by NIR were then used to estimate VFC, as the difference between the animal's capacity to use energy (as defined by Weston and Davis, 1991) and FCC. These data are summarised in Table 8.

VFC predicted in this way explained most of the variation in actual VFC (R=0.87; RSD=5.04; P=0.023) (FIG. 5).

TABLE 1

Description of herbage used in this example.

| Genus | Species | Variety | Common name | Part of plant | Process undergone | Stage of maturity | Regrowth |
|---|---|---|---|---|---|---|---|
| Panicum | coloratum | Bambatal | Makarikari grass | aerial | dried and chaffed | late bloom (9 weeks' regrowth) | late bloom - regrowth |
| Panicum | coloratum | Bambatal | Makarikari grass | aerial | dried and chaffed | late bloom (13 weeks' regrowth) | late bloom - regrowth |
| Panicum | coloratum | Bambatal | Makarikari grass | aerial | dried and chaffed | late bloom (4 weeks' regrowth) | late bllom - regrowth |
| Panicum | coloratum | Bambatal | Makarikari grass | aerial | dried and chaffed | mid bloom (1 month's regrowth) | mid bloom -regrowth |
| Panicum | coloratum | Bambatal | Makarikari grass | aerial | dried and chaffed | mid bloom (10 weeks' regrowth) | mid bloom - regrowth |
| Panicum | coloratum | Bambatal | Makarikari grass | aerial | dried and chaffed | mid bloom (6 weeks' regrowth) | mid bloom - regrowth |
| Panicum | coloratum | Bambatal | Makarikari grass | aerial | dried and chaffed | vegetative regrowth (29 days') | vegetative regrowth |
| Panicum | coloratum | Kabulabula CPI 16796 | Makarikari grass | aerial | dried and chaffed | late bloom | late bloom |
| Panicum | coloratum | Kabulabula CPI 16796 | Makarikari grass | aerial | dried and chaffed | late bloom (4 weeks' regrowth) | late bloom - regrowth |
| Panicum | coloratum | Kabulabula CPI 16796 | Makarikari grass | aerial | dried and chaffed | late bloom (19 weeks' regrowth) | late bloom - regrowth |
| Panicum | coloratum | Kabulabula CPI 16796 | Makarikari grass | aerial | dried and chaffed | late bloom (14 weeks' regrowth) | late bloom - regrowth |
| Panicum | coloratum | Kabulabula CPI 16796 | Makarikari grass | aerial | dried and chaffed | mid bloom 9 weeks' regrowth) | mid bloom - regrowth |
| Panicum | coloratum | Kabulabula CPI 16796 | Makarikari grass | aerial | dried and chaffed | mid bloom 6 weeks' regrowth) | mid bloom - regrowth |
| Panicum | coloratum | Kabulabula CPI 16796 | Makarikari grass | aerial | dried and chaffed | vegetative regrowth (28 days') | vegetative regrowth |
| Panicum | coloratum var Makarikariense | Burnett | Makarikari grass | aerial | dried and chaffed | early bloom (1 month's regrowth) | late bloom - regrowth |
| Panicum | coloratum var Makarikariense | Burnett | Makarikari grass | aerial | dried and chaffed | late bloom (14 weeks ' regrowth) | late bloom - regrowth |
| Panicum | coloratum var Makarikariense | Burnett | Makarikari grass | aerial | dried and chaffed | late bloom (4 weeks' regrowth) | late bloom - regrowth |
| Panicum | coloratum var Makarikariense | Burnett | Makarikari grass | aerial | dried and chaffed | mid bloom (8 weeks' regrowth) | mid bloom - regrowth |

TABLE 1-continued

Description of herbage used in this example.

| Genus | Species | Variety | Common name | Part of plant | Process undergone | Stage of maturity | Regrowth |
|---|---|---|---|---|---|---|---|
| Panicum | *coloratum* var Makarikariense | Burnett | Makarikari grass | aerial | dried and chaffed | mid bloom (10 weeks' regrowth) | mid bloom - regrowth |
| Panicum | *coloratum* var Makarikariense | Burnett | Makarikari grass | aerial | dried and chaffed | vegetative regrowth (31 days') | vegetative regrowth |
| Panicum | *coloratum* var Makarikariense | Burnett | Makarikari grass | aerial | dried and chaffed | mid bloom (1 month's regrowth) | mid bloom - regrowth |
| Panicum | *coloratum* var Makarikariense | Burnett | Makarikari grass | aerial | dried and chaffed | mid bloom (4 weeks' regrowth) | mid bloom - regrowth |
| Panicum | *maximum* | Coloniso | Guinea grass | aerial | dried and chaffed | late bloom (4 weeks' regrowth) | late bloom - regrowth |
| Panicum | *maximum* | Coloniso | Guinea grass | aerial | dried and chaffed | mid bloom (13 weeks' regrowth) | mid bloom - regrowth |
| Panicum | *maximum* | Coloniso | Guinea grass | aerial | dried and chaffed | mid bloom (10 weeks' regrowth) | mid bloom - regrowth |
| Panicum | *maximum* | Coloniso | Guinea grass | aerial | dried and chaffed | vegetative regrowth (4 weeks') | vegetative regrowth |
| Panicum | *maximum* | Coloniso | Guinea grass | aerial | dried and chaffed | vegetative regrowth (33 days') | vegetative regrowth |
| Panicum | *maximum* | Coloniso | Guinea grass | aerial | dried and chaffed | vegetative regrowth (28 days') | vegetative regrowth |
| Panicum | *maximum* | Coloniso | Guinea grass | aerial | dried and chaffed | vegetative regrowth (1 month's) | vegetative regrowth |
| Panicum | *maximum* | Coloniso | Guinea grass | aerial | dried and chaffed | vegetative regrowth (6 weeks') | vegetative regrowth |
| Panicum | *maximum* | Hamll | Guinea grass | aerial | dried and chaffed | early bloom (1 month's regrowth) | early bloom -regrowth |
| Panicum | *maximum* | Hamll | Guinea grass | aerial | dried and chaffed | early bloom (10 weeks' regrowth) | early bloom - regrowth |
| Panicum | *maximum* | Hamll | Guinea grass | aerial | dried and chaffed | late bloom (4 weeks' regrowth) | late bloom - regrowth |
| Panicum | *maximum* | Hamll | Guinea grass | aerial | dried and chaffed | mid bloom (13 weeks' regrowth) | mid bloom - regrowth |
| Panicum | *maximum* | Hamll | Guinea grass | leaf | dried and chaffed | 54 days' regrowth | regrowth |
| Panicum | *maximum* | Hamll | Guinea grass | leaf | dried and chaffed | 75 days' regrowth | regrowth |
| Panicum | *maximum* | Hamll | Guinea grass | leaf | dried and chaffed | 68 days' regrowth | regrowth |
| Panicum | *maximum* | Hamll | Guinea grass | aerial | dried and chaffed | vegetative (8 weeks' regrowth) | vegetative |
| Panicum | *maximum* | Hamll | Guinea grass | aerial | dried and chaffed | vegetative regrowth (9 weeks') | vbegetative regrowth |
| Panicum | *maximum* | Hamll | Guinea grass | aerial | dried and chaffed | vegetative regrowth (32 days') | vegetative regrowth |
| Panicum | *maximum* var. trichoglume | Petrie | Green Panlo | aerial | dried and chaffed | late bloom (6 weeks' regrowth) | late bloom - regrowth |
| Panicum | *maximum* var. trichoglume | Petrie | Green Panlo | aerial | dried and chaffed | mid bloom (1 month's regrowth) | mid bloom - regrowth |
| Panicum | *maximum* var. trichoglume | Petrie | Green Panlo | aerial | dried and chaffed | mid bloom (10 weeks' regrowth) | mid bloom - regrowth |
| Panicum | *maximum* var. trichoglume | Petrie | Green Panlo | aerial | dried and chaffed | mid bloom (14 weeks' regrowth) | mid bloom - regrowth |
| Panicum | *maximum* var. trichoglume | Petrie | Green Panlo | aerial | dried and chaffed | mid bloom (4 weeks' regrowth) | mid bloom - regrowth |
| Panicum | *maximum* var. trichoglume | Petrie | Green Panlo | aerial | dried and chaffed | mid bloom (15 weeks' regrowth) | mid bloom - regrowth |
| Panicum | *maximum* var. trichoglume | Petrie | Green Panlo | aerial | dried and chaffed | mid bloom (9 weeks' regrowth) | mid bloom - regrowth |
| Panicum | *maximum* var. trichoglume | Petrie | Green Panlo | aerial | dried and chaffed | mid bloom (1 month's) | mid bloom - regrowth |
| Panicum | *maximum* var. trichoglume | Petrie | Green Panlo | aerial | dried and chaffed | mid bloom (13 weeks' regrowth) | mid bloom - regrowth |
| Panicum | *maximum* var. trichoglume | Petrie | Green Panlo | aerial | dried and chaffed | mid bloom (4 weeks' regrowth) | mid bloom - regrowth |
| Panicum | *maximum* var. trichoglume | Petrie | Green Panlo | aerial | dried and chaffed | mid bloom (11 weeks' regrowth) | mid bloom - regrowth |
| Panicum | *maximum* var. trichoglume | Petrie | Green Panlo | aerial | dried and chaffed | vegetative regrowth (28 days') | vegetative regrowth |
| Panicum | *maximum* var. trichoglume | Petrie | Green Panlo | aerial | dried and chaffed | vegetative regrowth (32 days') | vegetative regrowth |
| Panicum | *maximum* var. trichoglume | Petrie | Green Panlo | aerial | dried and chaffed | vegetative regrowth (4 weeks') | vegetative regrowth |
| Panicum | *maximum* var. trichoglume | Petrie | Green Panlo | aerial | dried and chaffed | vegetative regrowth (4 weeks') | vegetative regrowth |

TABLE 2

Summary statistics for each calibration and validation set

| | Energy required to shear (kJ/m$^2$) | Energy required to comminute (kJ/kg DM) | Energy required to compress (kJ/kg DM) | Digestibility of dry matter in vivo (%) | Digestibility of dry matter in vitro (%) |
|---|---|---|---|---|---|
| | | | Energy required to shear | | |
| Calibration set | | | | | |
| mean | 15.48 | 134.9 | 3.70 | 55.7 | 53.3 |
| median | 15.17 | 133.8 | 3.65 | 56.0 | 55.1 |

TABLE 2-continued

Summary statistics for each calibration and validation set

| | Energy required to shear (kJ/m$^2$) | Energy required to comminute (kJ/kg DM) | Energy required to compress (kJ/kg DM) | Digestibility of dry matter in vivo (%) | Digestibility of dry matter in vitro (%) |
|---|---|---|---|---|---|
| maximum | 20.95 | 216.5 | 4.39 | 64.0 | 63.0 |
| minimum | 10.80 | 72.5 | 3.25 | 43.0 | 39.8 |
| standard deviation | 2.572 | 37.50 | 0.265 | 5.73 | 6.97 |
| Validation set | | | | | |
| mean | 15.43 | 130.9 | 3.78 | 55.6 | 52.7 |
| median | 15.20 | 128.3 | 3.75 | 56.5 | 53.3 |
| maximum | 20.43 | 205.2 | 4.24 | 64.0 | 63.0 |
| minimum | 10.94 | 54.5 | 3.34 | 47.0 | 40.1 |
| standard deviation | 2.444 | 37.50 | 0.229 | 5.36 | 7.01 |
| Energy required to comminute | | | | | |
| Calibration set | | | | | |
| mean | 15.01 | 133.1 | 3.69 | 55.7 | 52.8 |
| median | 14.76 | 129.5 | 3.70 | 57.0 | 54.7 |
| maximum | 19.97 | 216.5 | 4.18 | 64.0 | 63.0 |
| minimum | 10.80 | 54.5 | 3.25 | 43.0 | 39.8 |
| standard deviation | 2.444 | 38.82 | 0.227 | 5.64 | 7.06 |
| Validation set | | | | | |
| mean | 15.92 | 132.9 | 3.79 | 55.6 | 53.2 |
| median | 15.97 | 130.2 | 3.79 | 55.5 | 54.7 |
| maximum | 20.95 | 205.2 | 4.39 | 64.0 | 62.5 |
| minimum | 11.48 | 60.7 | 3.34 | 47.0 | 40.9 |
| standard deviation | 2.490 | 36.20 | 0.263 | 5.47 | 6.92 |
| Energy required to compress | | | | | |
| Calibration set | | | | | |
| mean | 15.28 | 128.1 | 3.74 | 56.3 | 53.8 |
| median | 15.07 | 128.4 | 3.72 | 57.0 | 54.7 |
| maximum | 19.97 | 204.0 | 4.39 | 64.0 | 63.0 |
| minimum | 10.80 | 54.5 | 3.25 | 47.0 | 39.8 |
| standard deviation | 2.477 | 38.00 | 0.261 | 5.15 | 6.64 |
| Validation set | | | | | |
| mean | 15.64 | 138.0 | 3.74 | 55.0 | 52.2 |
| median | 15.42 | 132.5 | 3.72 | 54.5 | 54.5 |
| maximum | 20.95 | 216.5 | 4.24 | 64.0 | 62.0 |
| minimum | 11.46 | 60.7 | 3.34 | 43.0 | 40.1 |
| standard deviation | 2.530 | 36.39 | 0.240 | 5.87 | 7.26 |
| Digestibility of dry matter in vivo | | | | | |
| Calibration set | | | | | |
| mean | 15.14 | 133.9 | 3.74 | 55.5 | 53.1 |
| median | 15.17 | 128.4 | 3.72 | 56.0 | 55.1 |
| maximum | 20.95 | 216.5 | 4.24 | 64.0 | 63.0 |
| minimum | 10.80 | 60.7 | 3.25 | 43.0 | 40.1 |
| standard deviation | 2.528 | 36.39 | 0.247 | 5.73 | 7.33 |
| Validation set | | | | | |
| mean | 15.78 | 132.1 | 3.75 | 55.7 | 52.9 |
| median | 15.20 | 134.7 | 3.72 | 56.5 | 54.4 |
| maximum | 20.37 | 205.2 | 4.39 | 64.0 | 63.0 |
| minimum | 10.94 | 54.5 | 3.34 | 47.0 | 39.8 |
| standard deviation | 2.446 | 38.70 | 0.255 | 5.36 | 6.63 |
| Digestibility of dry matter in vitro | | | | | |
| Calibration set | | | | | |
| mean | 14.70 | 131.3 | 3.75 | 55.6 | 53.0 |
| median | 14.34 | 129.3 | 3.71 | 56.0 | 54.7 |
| maximum | 19.36 | 216.5 | 4.39 | 64.0 | 63.0 |
| minimum | 10.80 | 54.5 | 3.25 | 43.0 | 40.1 |
| standard deviation | 2.235 | 42.58 | 0.241 | 5.78 | 6.94 |
| Validation set | | | | | |
| mean | 16.19 | 134.6 | 3.74 | 55.6 | 53.0 |
| median | 16.16 | 133.8 | 3.74 | 56.0 | 54.7 |

TABLE 2-continued

Summary statistics for each calibration and validation set

|  | Energy required to shear (kJ/m$^2$) | Energy required to comminute (kJ/kg DM) | Energy required to compress (kJ/kg DM) | Digestibility of dry matter in vivo (%) | Digestibility of dry matter in vitro (%) |
|---|---|---|---|---|---|
| maximum | 20.95 | 194.8 | 4.24 | 64.0 | 63.0 |
| minimum | 10.94 | 65.7 | 3.34 | 47.0 | 39.8 |
| standard deviation | 2.538 | 31.84 | 0.260 | 5.33 | 7.05 |

TABLE 3

Mahalanobis distances

|  | Mean | Median | Range |
|---|---|---|---|
| For full sample set: | 0.655 | 0.623 | 0.203–1.983 |
| For calibration sets for: |  |  |  |
| Energy required to shear | 0.588 | 0.549 | 0.171–1.646 |
| Energy required to comminute | 0.718 | 0.676 | 0.350–1.553 |
| Energy required to compress | 0.757 | 0.760 | 0.188–1.440 |
| Digestibility of dry matter in vivo | 0.673 | 0.634 | 0.389–1.547 |
| Digestibility of dry matter in vitro | 0.645 | 0.574 | 0.185–1.178 |

TABLE 4a

Calibration and validation statistics

|  | Stepwise Regression | | | |
|---|---|---|---|---|
|  | 2,2,2 | 2,5,5 | 2,10,5 | 2,10,10 |
| Energy required to shear | | | | |
| Lowest partial F-ratio | 10.27 | 6.18 | 8.27 | 4.70 |
| R$^2$ | 0.798 | 0.787 | 0.795 | 0.780 |
| SEC | 1.155 | 1.188 | 1.166 | 1.207 |
| SEC CL | 1.493 | 1.535 | 1.507 | 1.560 |
| SEV(C) | 1.230 | 1.306 | 1.273 | 1.322 |
| r$^2$ | 0.368 | 0.625 | 0.520 | 0.495 |
| Bias | 0.690 | 0.710 | 0.700 | 0.720 |
| Bias CL | 1.484 | 1.527 | 1.498 | 1.551 |
| SEP (C) | 1.500 | 1.540 | 1.520 | 1.570 |
| Slope | 0.604 | 0.617 | 0.598 | 0.758 |
| Intercept | 6.340 | 5.440 | 5.640 | 3.710 |
| R.S.D. | 1.627 | 1.627 | 1.484 | 1.476 |
| \|Bias\| - Bias CL | -0.794 | 0.817 | 0.798 | 0.831 |
| \|Bias\| < Bias CL? | Yes | Yes | Yes | Yes |
| number of terms | 6 | 5 | 5 | 6 |
| Energy required to comminute | | | | |
| Lowest partial F-ratio | 5.54 | 4.45 | 16.55 | 10.89 |
| R$^2$ | 0.910 | 0.802 | 0.818 | 0.831 |
| SEC | 11.626 | 17.281 | 16.546 | 15.980 |
| SEC CL | 1.493 | 1.535 | 1.507 | 1.560 |
| SEV(C) | 13.103 | 18.040 | 17.587 | 17.100 |
| r$^2$ | 0.363 | 0.429 | 0.374 | 0.213 |
| Bias | 6.980 | 10.370 | 9.930 | 9.590 |
| Bias CL | 14.941 | 22.209 | 21.264 | 20.537 |
| SEP (C) | 15.110 | 22.460 | 21.510 | 20.770 |
| Slope | 0.530 | 0.575 | 0.607 | 0.417 |
| Intercept | 58.300 | 48.900 | 48.600 | 74.600 |
| R.S.D. | 28.900 | 27.360 | 28.650 | 32.120 |
| \|Bias\| - Bias CL | -7.961 | -11.839 | -11.334 | -10.947 |
| \|Bias\| < Bias CL? | Yes | Yes | Yes | Yes |
| number of terms | 6 | 3 | 4 | 4 |
| Energy required to compress | | | | |
| Lowest partial F-ratio | 5.05 | 4.44 | 7.90 | 16.19 |
| R$^2$ | 0.784 | 0.500 | 0.525 | 0.534 |
| SEC | 0.121 | 0.209 | 0.204 | 0.202 |
| SEC CL | 1.493 | 1.535 | 1.507 | 1.560 |
| SEV(C) | 0.135 | 0.224 | 0.217 | 0.215 |
| r$^2$ | 0.069 | 0.113 | 0.008 | 0.067 |
| Bias | 0.070 | 0.130 | 0.120 | 0.120 |
| Bias CL | 0.156 | 0.269 | 0.262 | 0.260 |
| SEP (C) | 0.160 | 0.270 | 0.270 | 0.260 |
| Slope | 0.180 | -0.080 | 0.314 | 0.211 |
| Intercept | 3.060 | 4.030 | 2.580 | 2.960 |
| R.S.D. | 0.229 | 0.229 | 0.227 | 0.232 |
| \|Bias\| - Bias CL | -0.086 | -0.139 | -0.142 | -0.140 |
| \|Bias\| < Bias CL? | Yes | Yes | Yes | Yes |
| number of terms | 6 | 4 | 4 | 4 |
| Digestibility of dry matter in vivo | | | | |
| Lowest partial F-ratio | 7.63 | 20.68 | 4.28 | 6.08 |
| R$^2$ | 0.934 | 0.917 | 0.914 | 0.921 |
| SEC | 1.107 | 1.236 | 1.258 | 1.207 |
| SEC CL | 1.493 | 1.535 | 1.507 | 1.560 |
| SEV(C) | 1.215 | 1.368 | 1.341 | 1.284 |
| r$^2$ | 0.654 | 0.881 | 0.878 | 0.876 |
| Bias | 1.070 | 0.890 | 0.910 | 0.900 |
| Bias CL | 0.156 | 0.269 | 0.262 | 0.260 |
| SEP (C) | 2.320 | 1.940 | 1.980 | 1.960 |
| Slope | 0.705 | 0.878 | 0.840 | 0.827 |
| Intercept | 16.500 | 6.690 | 8.640 | 9.340 |
| R.S.D. | 3.153 | 1.852 | 1.873 | 1.888 |
| \|Bias\| - Bias CL | 0.914 | 0.621 | 0.648 | 0.640 |
| \|Bias\| < Bias CL? | No | No | No | No |
| number of terms | 6 | 6 | 6 | 5 |

|  | Stepwise Regression | | | |
|---|---|---|---|---|
|  | 2,2,2,1 | 2,5,5 | 2,10,5 | 2,10,10 |
| Digestibility of dry matter in vitro | | | | |
| Lowest partial F-ratio | 7.68 | 11.84 | 4.33 | 6.31 |
| R$^2$ | 0.935 | 0.933 | 0.915 | 0.922 |
| SEC | 1.808 | 1.751 | 2.052 | 1.974 |
| SEC CL | 1.493 | 1.535 | 1.507 | 1.560 |
| SEV(C) | 1.984 | 1.981 | 2.186 | 2.100 |
| r$^2$ | 0.699 | 0.847 | 0.743 | 0.736 |
| Bias | 1.080 | 1.050 | 1.230 | 1.180 |
| Bias CL | 2.324 | 2.250 | 2.637 | 2.537 |
| SEP (C) | 2.340 | 2.280 | 2.670 | 2.570 |
| Slope | 0.839 | 0.962 | 0.775 | 0.763 |
| Intercept | 8.790 | 1.650 | 12.200 | 12.700 |
| R.S.D. | 3.805 | 3.794 | 3.805 | 2.719 |
| \|Bias\| - Bias CL | -1.244 | -1.200 | -1.407 | -1.357 |
| \|Bias\| < Bias CL? | Yes | Yes | Yes | Yes |
| number of terms | 6 | 5 | 6 | 5 |

TABLE 4b

Calibration and validation statistics (Step-up regression)

| | Step-up Regression 2, 2, 2 | | | | | | Step-up Regression 2, 5, 5 | | | | | |
|---|---|---|---|---|---|---|---|---|---|---|---|---|
| | 1 term | 2 terms | 3 terms | 4 terms | 5 terms | 6 terms | 1 term | 2 terms | 3 terms | 4 terms | 5 terms | 6 terms |

Energy required to shear

| | | | | | | | | | | | | |
|---|---|---|---|---|---|---|---|---|---|---|---|---|
| Lowest partial F-ratio | 29.33 | 13.83 | 6.65 | 5.29 | 5.89 | 3.23 | 25.70 | 21.99 | 5.71 | 1.60 | 4.92 | 1.70 |
| $R^2$ | 0.470 | 0.625 | 0.684 | 0.725 | 0.766 | 0.784 | 0.436 | 0.663 | 0.709 | 0.715 | 0.778 | 0.792 |
| SEC | 1.873 | 1.575 | 1.445 | 1.349 | 1.244 | 1.196 | 1.932 | 1.492 | 1.387 | 1.373 | 1.211 | 1.173 |
| SEC CL | 2.420 | 2.035 | 1.867 | 1.743 | 1.608 | 1.546 | 2.497 | 1.928 | 1.792 | 1.774 | 1.565 | 1.516 |
| SEV (C) | 1.973 | 1.672 | 1.561 | 1.476 | 1.390 | 1.318 | 2.022 | 1.571 | 1.476 | 1.470 | 1.357 | 1.319 |
| $r^2$ | 0.371 | 0.344 | 0.310 | 0.205 | 0.202 | 0.168 | 0.375 | 0.531 | 0.557 | 0.557 | 0.631 | 0.635 |
| Bias | 1.120 | 0.950 | 0.870 | 0.810 | 0.775 | 0.720 | 1.160 | 0.900 | 0.830 | 0.820 | 0.730 | 0.700 |
| Bias CL | 2.407 | 2.024 | 1.857 | 1.734 | 1.599 | 1.537 | 2.483 | 1.917 | 1.783 | 1.765 | 1.556 | 1.507 |
| SEP (C) | 2.430 | 2.050 | 1.880 | 1.750 | 1.620 | 1.550 | 2.510 | 1.940 | 1.800 | 1.780 | 1.570 | 1.520 |
| Slope | 1.000 | 0.795 | 0.784 | 0.598 | 0.549 | 0.498 | 0.643 | 0.606 | 0.616 | 0.633 | 0.644 | 0.633 |
| Intercept | −0.120 | 3.030 | 3.290 | 6.090 | 6.950 | 7.790 | 6.390 | 5.790 | 5.560 | 5.270 | 5.050 | 5.170 |
| R.S.D. | 1.896 | 1.803 | 1.773 | 1.769 | 1.732 | 2.058 | 1.891 | 1.806 | 1.698 | 1.656 | 2.317 | 1.945 |
| \|Bias\| − Bias CL | −1.287 | −1.074 | −0.987 | −0.924 | −0.824 | −0.817 | −1.323 | −1.017 | −0.953 | −0.945 | −0.826 | −0.807 |
| \|Bias\| < Bias CL? | Yes | Yes | Yes | Yes | Yes | Yes | Yes | Yes | Yes | Yes | Yes | Yes |

Energy required to comminute

| | | | | | | | | | | | | |
|---|---|---|---|---|---|---|---|---|---|---|---|---|
| Lowest partial F-ratio | 81.33 | 12.82 | 9.62 | 6.10 | 6.71 | 2.92 | 67.30 | 8.96 | 2.73 | 4.91 | 5.06 | 4.26 |
| $R^2$ | 0.715 | 0.794 | 0.840 | 0.864 | 0.887 | 0.894 | 0.974 | 0.741 | 0.755 | 0.782 | 0.810 | 0.830 |
| SEC | 20.719 | 17.829 | 15.538 | 14.330 | 13.061 | 12.620 | 22.149 | 19.757 | 19.213 | 18.105 | 16.921 | 15.983 |
| SEC CL | 2.420 | 2.035 | 1.867 | 1.743 | 1.608 | 1.546 | 2.497 | 1.928 | 1.792 | 1.774 | 1.565 | 1.516 |
| SEV (C) | 21.511 | 18.353 | 16.378 | 15.230 | 13.967 | 13.633 | 22.769 | 20.547 | 20.096 | 19.092 | 18.262 | 17.484 |
| $r^2$ | 0.322 | 0.424 | 0.421 | 0.411 | 0.371 | 0.373 | 0.183 | 0.199 | 0.148 | 0.099 | 0.114 | 0.098 |
| Bias | 12.430 | 10.580 | 9.320 | 8.600 | 7.840 | 7.570 | 13.290 | 11.850 | 11.530 | 10.860 | 10.150 | 9.590 |
| Bias CL | 26.627 | 22.656 | 19.969 | 18.416 | 16.785 | 16.219 | 28.465 | 25.391 | 24.692 | 23.268 | 21.746 | 20.541 |
| SEP (C) | 26.940 | 22.920 | 20.200 | 18.630 | 16.980 | 16.410 | 28.790 | 25.680 | 24.980 | 23.540 | 22.000 | 20.780 |
| Slope | 0.605 | 0.623 | 0.577 | 0.560 | 0.524 | 0.521 | 0.491 | 0.518 | 0.441 | 0.346 | 0.365 | 0.317 |
| Intercept | 47.100 | 43.900 | 48.900 | 52.900 | 58.300 | 57.800 | 60.100 | 58.500 | 70.800 | 84.600 | 82.700 | 89.600 |
| R.S.D. | 29.810 | 27.480 | 27.550 | 27.790 | 28.720 | 28.670 | 32.400 | 32.400 | 33.420 | 34.370 | 34.070 | 34.380 |
| \|Bias\| − Bias CL | −14.197 | −12.076 | −9.816 | −8.945 | −8.649 | −15.175 | −13.541 | −13.162 | −12.408 | −11.596 | −10.951 | |
| \|Bias\| < Bias CL? | Yes | Yes | Yes | Yes | Yes | Yes | Yes | Yes | Yes | Yes | Yes | Yes |

Energy required to compress

| | | | | | | | | | | | | |
|---|---|---|---|---|---|---|---|---|---|---|---|---|
| Lowest partial F-ratio | 7.28 | 6.24 | 3.22 | 2.65 | 3.10 | 0.00 | 8.07 | 4.23 | 4.08 | 2.21 | 5.36 | 1.87 |
| $R^2$ | 0.164 | 0.285 | 0.334 | 0.370 | 0.440 | 0.530 | 0.181 | 0.258 | 0.327 | 0.445 | 0.520 | 0.535 |
| SEC | 0.270 | 0.250 | 0.241 | 0.235 | 0.221 | 0.203 | 0.268 | 0.255 | 0.243 | 0.220 | 0.205 | 0.202 |
| SEC CL | 2.420 | 2.035 | 1.867 | 1.743 | 1.608 | 1.546 | 2.497 | 1.928 | 1.792 | 1.774 | 1.565 | 1.518 |
| SEV (C) | 0.277 | 0.259 | 0.252 | 0.248 | 0.238 | 0.226 | 0.276 | 0.268 | 0.257 | 0.241 | 0.227 | 0.222 |
| $r^2$ | 0.067 | 0.089 | 0.087 | 0.104 | 0.067 | 0.033 | 0.039 | 0.064 | 0.038 | 0.005 | 0.010 | 0.006 |
| Bias | 0.160 | 0.150 | 0.140 | 0.140 | 0.130 | 0.120 | 0.160 | 0.150 | 0.150 | 0.130 | 0.120 | 0.120 |
| Bias CL | 0.347 | 0.321 | 0.310 | 0.302 | 0.284 | 0.261 | 0.344 | 0.328 | 0.312 | 0.283 | 0.263 | 0.260 |
| SEP (C) | 0.350 | 0.330 | 0.310 | 0.310 | 0.290 | 0.260 | 0.350 | 0.330 | 0.320 | 0.290 | 0.270 | 0.260 |
| Slope | 0.367 | 0.394 | 0.345 | 0.341 | 0.280 | 0.156 | 0.267 | 0.295 | 0.198 | 0.068 | 0.085 | 0.063 |
| Intercept | 2.380 | 2.270 | 2.460 | 2.470 | 2.690 | 3.160 | 2.750 | 2.640 | 3.010 | 3.490 | 3.420 | 3.510 |
| R.S.D. | 0.235 | 0.232 | 0.235 | 0.239 | 0.239 | 0.239 | 0.236 | 0.233 | 0.230 | 0.229 | 0.233 | 0.239 |
| \|Bias\| − Bias CL | −0.187 | −0.171 | −0.170 | −0.162 | −0.154 | −0.141 | −0.184 | −0.178 | −0.162 | −0.153 | −0.143 | −0.140 |
| \|Bias\| < Bias CL? | Yes | Yes | Yes | Yes | Yes | Yes | Yes | Yes | Yes | Yes | Yes | Yes |

Digestibility of dry matter in vivo

| | | | | | | | | | | | | |
|---|---|---|---|---|---|---|---|---|---|---|---|---|
| Lowest partial F-ratio | 72.42 | 5.79 | 8.71 | 16.80 | 13.18 | 2.86 | 80.75 | 12.35 | 8.41 | 7.34 | 6.03 | 3.72 |
| $R^2$ | 0.616 | 0.714 | 0.830 | 0.862 | 0.883 | 0.906 | 0.679 | 0.826 | 0.897 | 0.909 | 0.919 | 0.924 |
| SEC | 3.555 | −3.069 | 2.365 | 2.127 | 1.962 | 1.755 | 3.248 | 2.394 | 1.840 | 1.728 | 1.635 | 1.588 |
| SEC CL | 2.420 | 2.035 | 1.867 | 1.743 | 1.608 | 1.546 | 2.497 | 1.928 | 1.792 | 1.774 | 1.565 | 1.516 |
| SEV (C) | 3.666 | 3.250 | 2.447 | 2.312 | 2.152 | 1.956 | 3.328 | 2.457 | 1.972 | 1.884 | 1.828 | 1.782 |
| $r^2$ | 0.785 | 0.712 | 0.684 | 0.787 | 0.884 | 0.768 | 0.755 | 0.740 | 0.884 | 0.893 | 0.876 | 0.869 |
| Bias | 2.130 | 1.840 | 1.420 | 1.280 | 1.180 | 1.050 | 1.950 | 1.440 | 1.100 | 1.040 | 0.980 | 0.950 |
| Bias CL | 0.347 | 0.321 | 0.310 | 0.302 | 0.284 | 0.261 | 0.344 | 0.328 | 0.312 | 0.283 | 0.263 | 0.260 |
| SEP (C) | 4.620 | 3.990 | 3.070 | 2.770 | 2.550 | 2.280 | 4.220 | 3.110 | 2.390 | 2.250 | 2.130 | 2.060 |
| Slope | 1.050 | 0.805 | 0.792 | 0.826 | 0.777 | 0.731 | 1.090 | 1.050 | 0.889 | 0.880 | 0.866 | 0.885 |
| Intercept | −2.180 | 10.300 | 11.000 | 9.040 | 11.900 | 14.900 | −5.290 | −3.300 | 5.850 | 6.430 | 7.210 | 6.080 |
| R.S.D. | 2.484 | 2.877 | 2.584 | 2.652 | 2.734 | 3.108 | 2.476 | 1.825 | 1.825 | 1.750 | 1.884 | 1.940 |
| \|Bias\| − Bias CL | 1.783 | 1.519 | 1.110 | 0.978 | 0.896 | 0.789 | 1.606 | 1.112 | 0.788 | 0.757 | 0.717 | 0.690 |
| \|Bias\| < Bias CL? | No | No | No | No | No | No | No | No | No | No | No | No |

Digestibility of dry matter in vitro

| | | | | | | | | | | | | |
|---|---|---|---|---|---|---|---|---|---|---|---|---|
| Lowest partial F-ratio | 73.30 | 5.73 | 8.71 | 17.00 | 13.23 | 2.99 | 81.21 | 12.38 | 8.48 | 7.23 | 6.07 | 3.72 |
| $R^2$ | 0.692 | 0.733 | 0.788 | 0.905 | 0.915 | 0.715 | 0.791 | 0.833 | 0.863 | 0.884 | 0.894 | |
| SEC | 3.913 | 3.645 | 2.251 | 2.610 | 2.177 | 2.058 | 3.768 | 3.222 | 2.883 | 2.818 | 2.407 | 2.294 |
| SEC CL | 2.420 | 2.035 | 1.867 | 1.743 | 1.608 | 1.546 | 2.497 | 1.928 | 1.792 | 1.774 | 1.565 | 1.516 |
| SEV (C) | 4.020 | 3.186 | 3.411 | 2.a781 | 2.324 | 2.203 | 3.855 | 3.360 | 3.063 | 2.809 | 2.615 | 2.490 |
| $r^2$ | 0.731 | 0.694 | 0.687 | 0.644 | 0.685 | 0.671 | 0.735 | 0.856 | 0.845 | 0.849 | 0.801 | 0.800 |
| Bias | 2.350 | 2.190 | 1.950 | 1.570 | 1.310 | 1.230 | 2.260 | 1.930 | 1.730 | 1.570 | 1.440 | 1.380 |

TABLE 4b-continued

Calibration and validation statistics (Step-up regression)

| | | | | | | | | | | | | |
|---|---|---|---|---|---|---|---|---|---|---|---|---|
| Bias CL | 5.029 | 4.684 | 2.893 | 3.354 | 2.798 | 2.645 | 4.842 | 4.141 | 3.705 | 3.362 | 3.093 | 2.948 |
| SEP (C) | 5.090 | 4.740 | 4.230 | 3.390 | 2.830 | 2.680 | 4.900 | 4.190 | 3.750 | 3.400 | 3.130 | 2.980 |
| Slope | 0.946 | 0.868 | 0.861 | 0.877 | 0.860 | 0.830 | 1.080 | 0.994 | 1.020 | 0.976 | 0.975 | 0.914 |
| Intercept | 2.000 | 5.890 | 6.550 | 6.140 | 7.240 | 9.150 | -4.700 | -0.410 | -1.970 | 0.240 | 0.240 | 4.040 |
| R.S.D. | 3.565 | 3.601 | 3.842 | 3.882 | 4.143 | 3.895 | 3.576 | 2.637 | 2.733 | 2.694 | 3.097 | 3.103 |
| \|Bias\| − Bias CL | -2.879 | -2.494 | -0.943 | -1.784 | -1.488 | -1.415 | -2.582 | -2.211 | -1.975 | -1.792 | -1.653 | -1.568 |
| \|Bias\| < Bias CL? | Yes | Yes | Yes | Yes | Yes | Yes | Yes | Yes | Yes | Yes | Yes | Yes |

| | Step-up Regression 2,10,5 | | | | | | Step-up Regression 2, 10, 10 | | | | | |
|---|---|---|---|---|---|---|---|---|---|---|---|---|
| | 1 term | 2 terms | 3 terms | 4 terms | 5 terms | 6 terms | 1 term | 2 terms | 3 terms | 4 terms | 5 terms | 6 terms |

Energy required to shear

| | | | | | | | | | | | | |
|---|---|---|---|---|---|---|---|---|---|---|---|---|
| Lowest partial F-ratio | 25.11 | 14.92 | 5.87 | 4.42 | 7.81 | 1.89 | 23.54 | 15.23 | 4.01 | 4.30 | 4.35 | 4.66 |
| $R^2$ | 0.430 | 0.606 | 0.661 | 0.697 | 0.755 | 0.763 | 0.413 | 0.598 | 0.641 | 0.678 | 0.721 | 0.755 |
| SEC | 1.942 | 1.613 | 1.496 | 1.415 | 1.273 | 1.252 | 1.970 | 1.631 | 1.541 | 1.460 | 1.358 | 1.274 |
| SEC CL | 2.510 | 2.084 | 1.933 | 1.829 | 1.645 | 1.618 | 2.546 | 2.108 | 1.991 | 1.887 | 1.755 | 1.646 |
| SEV (C) | 2.020 | 1.674 | 1.611 | 1.541 | 1.403 | 1.392 | 2.047 | 1.689 | 1.612 | 1.569 | 1.494 | 1.411 |
| $r^2$ | 0.273 | 0.398 | 0.456 | 0.473 | 0.476 | 0.498 | 0.291 | 0.333 | 0.401 | 0.454 | 0.517 | 0.541 |
| Bias | 1.170 | 0.970 | 0.900 | 0.850 | 0.760 | 0.750 | 1.180 | 0.980 | 0.920 | 0.880 | 0.810 | 0.760 |
| Bias CL | 2.496 | 2.073 | 1.923 | 1.818 | 1.636 | 1.609 | 2.532 | 2.096 | 1.980 | 1.876 | 1.745 | 1.637 |
| SEP (C) | 2.520 | 2.100 | 1.950 | 1.840 | 1.650 | 1.630 | 2.560 | 2.120 | 2.000 | 1.900 | 1.760 | 1.660 |
| Slope | 0.706 | 0.723 | 0.717 | 0.707 | 0.610 | 0.616 | 0.737 | 0.581 | 0.639 | 0.653 | 0.715 | 0.709 |
| Intercept | 4.150 | 3.950 | 4.320 | 4.260 | 5.620 | 5.440 | 3.720 | 5.850 | 5.040 | 5.040 | 4.130 | 4.160 |
| R.S.D. | 2.170 | 2.193 | 2.343 | 2.367 | 2.524 | 2.375 | 2.179 | 1.607 | 1.666 | 1.644 | 1.889 | 1.893 |
| \|Bias\| − Bias CL | -1.326 | -1.103 | -1.023 | -0.968 | -0.876 | -0.859 | -1.352 | -1.116 | -1.060 | -0.996 | -0.935 | -0.877 |
| \|Bias\| < Bias CL? | Yes | Yes | Yes | Yes | Yes | Yes | Yes | Yes | Yes | Yes | Yes | Yes |

Energy required to comminute

| | | | | | | | | | | | | |
|---|---|---|---|---|---|---|---|---|---|---|---|---|
| Lowest partial F-ratio | 76.72 | 5.31 | 2.76 | 2.18 | 1.68 | 1.01 | 74.65 | 5.39 | 2.13 | 2.96 | 4.38 | 1.49 |
| $R^2$ | 0.730 | 0.739 | 0.754 | 0.763 | 0.772 | 0.800 | 0.698 | 0.735 | 0.745 | 0.781 | 0.787 | 0.791 |
| SEC | 21.158 | 19.825 | 19.267 | 18.887 | 18.518 | 17.344 | 21.345 | 19.977 | 19.611 | 18.982 | 17.929 | 17.768 |
| SEC CL | 2.510 | 2.084 | 1.933 | 1.829 | 1.645 | 1.618 | 2.548 | 2.108 | 1.991 | 1.887 | 1.755 | 1.646 |
| SEV (C) | 21.803 | 20.707 | 20.279 | 19.690 | 19.499 | 18.691 | 22.033 | 20.904 | 20.985 | 19.911 | 18.777 | 18.634 |
| $r^2$ | 0.460 | 0.468 | 0.414 | 0.394 | 0.330 | 0.215 | 0.434 | 0.450 | 0.408 | 0.397 | 0.357 | 0.387 |
| Bias | 12.690 | 11.890 | 11.560 | 11.330 | 11.110 | 10.410 | 12.810 | 11.990 | 11.700 | 11.390 | 10.760 | 10.660 |
| Bias CL | 27.191 | 25.478 | 24.761 | 24.273 | 23.799 | 22.290 | 27.432 | 25.676 | 25.203 | 24.395 | 23.042 | 22.835 |
| SEP (C) | 27.510 | 25.770 | 25.050 | 24.550 | 24.070 | 22.550 | 27.750 | 25.970 | 25.490 | 24.680 | 23.310 | 23.100 |
| Slope | 0.793 | 0.737 | 0.688 | 0.649 | 0.598 | 0.468 | 0.776 | 0.729 | 0.694 | 0.645 | 0.622 | 0.633 |
| Intercept | 18.300 | 24.500 | 31.800 | 39.600 | 48.100 | 67.100 | 20.200 | 25.600 | 30.800 | 39.000 | 43.600 | 42.200 |
| R.S.D. | 26.610 | 26.420 | 27.720 | 28.170 | 29.640 | 32.080 | 27.230 | 26.850 | 27.860 | 28.100 | 29.030 | 28.350 |
| \|Bias\| − Bias CL | -14.501 | -13.588 | -13.201 | -12.943 | -12.689 | -11880 | -14.622 | -13.684 | -13.503 | -13.005 | -12.282 | -12.175 |
| \|Bias\| < Bias CL? | Yes | Yes | Yes | Yes | Yes | Yes | Yes | Yes | Yes | Yes | Yes | Yes |

Energy required to compress

| | | | | | | | | | | | | |
|---|---|---|---|---|---|---|---|---|---|---|---|---|
| Lowest partial F-ratio | 8.16 | 2.24 | 8.06 | 4.06 | 1.97 | 4.98 | 6.50 | 4.94 | 4.91 | 1.75 | 3.54 | 3.83 |
| $R^2$ | 0.183 | 0.214 | 0.364 | 0.457 | 0.532 | 0.592 | 0.147 | 0.243 | 0.397 | 0.412 | 0.461 | 0.512 |
| SEC | 0.267 | 0.262 | 0.236 | 0.218 | 0.202 | 0.189 | 0.273 | 0.257 | 0.230 | 0.227 | 0.217 | 0.207 |
| SEC CL | 2.510 | 2.084 | 1.933 | 1.829 | 1.645 | 1.618 | 2.546 | 2.108 | 1.991 | 1.887 | 1.755 | 1.646 |
| SEV (C) | 0.278 | 0.275 | 0.252 | 0.235 | 0.218 | 0.210 | 0.283 | 0.273 | 0.250 | 0.250 | 0.247 | 0.235 |
| $r^2$ | 0.010 | 0.028 | 0.052 | 0.076 | 0.086 | 0.053 | 0.006 | 0.057 | 0.045 | 0.052 | 0.035 | 0.029 |
| Bias | 0.160 | 0.160 | 0.140 | 0.130 | 0.120 | 0.110 | 0.160 | 0.150 | 0.140 | 0.140 | 0.130 | 0.120 |
| Bias CL | 0.343 | 0.337 | 0.303 | 0.280 | 0.260 | 0.243 | 0.351 | 0.330 | 0.300 | 0.290 | 0.280 | 0.270 |
| SEP (C) | 0.350 | 0.340 | 0.310 | 0.280 | 0.260 | 0.250 | 0.360 | 0.330 | 0.300 | 0.290 | 0.280 | 0.270 |
| Slope | 0.127 | 0.212 | 0.239 | 0.252 | 0.218 | 0.142 | 0.102 | 0.294 | 0.216 | 0.212 | 0.149 | 0.149 |
| Intercept | 3.270 | 2.960 | 2.850 | 2.800 | 2.930 | 3.210 | 3.360 | 2.640 | 2.940 | 2.950 | 3.180 | 3.190 |
| R.S.D. | 0.234 | 0.233 | 0.235 | 0.236 | 1.942 | 1.495 | 1.736 | 1.938 | 1.980 | 2.030 | 2.179 | 2.183 |
| \|Bias\| − Bias CL | -0.183 | -0.177 | -0.163 | -0.150 | -0.140 | -0.133 | -0.191 | -0.180 | -0.156 | -0.152 | -0.149 | -0.146 |
| \|Bias\| < Bias CL? | Yes | Yes | Yes | Yes | Yes | Yes | Yes | Yes | Yes | Yes | Yes | Yes |

Digestibility of dry matter in vivo

| | | | | | | | | | | | | |
|---|---|---|---|---|---|---|---|---|---|---|---|---|
| Lowest partial F-ratio | 91.59 | 9.46 | 9.77 | 7.10 | 2.58 | 4.12 | 93.60 | 6.52 | 16.07 | 4.36 | 4.68 | 4.94 |
| $R^2$ | 0.700 | 0.867 | 0.902 | 0.916 | 0.927 | 0.935 | 0.675 | 0.815 | 0.898 | 0.912 | 0.922 | 0.927 |
| SEC | 3.139 | 2.095 | 1.794 | 1.660 | 1.545 | 1.457 | 3.271 | 2.467 | 1.828 | 1.698 | 1.598 | 1.546 |
| SEC CL | 2.510 | 2.084 | 1.933 | 1.829 | 1.645 | 1.618 | 2.546 | 2.108 | 1.991 | 1.887 | 1.755 | 1.646 |
| SEV (C) | 3.332 | 2.282 | 1.997 | 1.830 | 1.694 | 1.607 | 3.357 | 2.572 | 2.016 | 1.905 | 1.840 | 1.787 |
| $r^2$ | 0.777 | 0.856 | 0.888 | 0.871 | 0.887 | 0.881 | 0.828 | 0.831 | 0.809 | 0.836 | 0.877 | 0.892 |
| Bias | 1.880 | 1.260 | 1.080 | 1.000 | 0.930 | 0.870 | 1.960 | 1.480 | 1.100 | 1.020 | 0.960 | 0.930 |
| Bias CL | 0.343 | 0.337 | 0.303 | 0.280 | 0.260 | 0.243 | 0.351 | 0.330 | 0.296 | 0.292 | 0.279 | 0.266 |
| SEP (C) | 4.080 | 2.720 | 2.330 | 2.160 | 2.010 | 1.890 | 4.250 | 3.210 | 2.380 | 2.210 | 2.080 | 2.010 |
| Slope | 0.892 | 0.880 | 0.924 | 0.870 | 0.851 | 0.837 | 1.130 | 0.991 | 0.812 | 0.829 | 0.840 | 0.865 |
| Intercept | 7.380 | 6.750 | 3.930 | 6.850 | 8.320 | 8.960 | -6.490 | 0.210 | 9.960 | 9.030 | 8.710 | 7.270 |
| R.S.D. | 2.531 | 2.034 | 1.791 | 1.927 | 1.799 | 1.848 | 2.222 | 2.201 | 2.344 | 2.172 | 1.876 | 1.761 |
| \|Bias\| − Bias CL | 1.537 | 0.923 | 0.777 | 0.720 | 0.670 | 0.627 | 1.609 | 1.150 | 0.804 | 0.728 | 0.681 | 0.664 |
| \|Bias\| < Bias CL? | No | No | No | No | No | No | No | No | No | No | No | No |

TABLE 4b-continued

Calibration and validation statistics (Step-up regression)

Digestibility of dry matter in vivo

| | | | | | | | | | | | | |
|---|---|---|---|---|---|---|---|---|---|---|---|---|
| Lowest partial F-ratio | 94.12 | 8.62 | 16.01 | 4.48 | 4.61 | 5.01 | 92.14 | 9.60 | 9.70 | 10.55 | 2.67 | 4.41 |
| $R^2$ | 0.744 | 0.784 | 0.856 | 0.871 | 0.886 | 0.901 | 0.740 | 0.797 | 0.842 | 0.881 | 0.888 | 0.900 |
| SEC | 3.568 | 3.283 | 2.680 | 2.532 | 2.384 | 2.224 | 3.598 | 3.182 | 2.802 | 2.430 | 2.351 | 2.235 |
| SEC CL | 2.510 | 2.084 | 1.933 | 1.829 | 1.645 | 1.618 | 2.546 | 2.108 | 1.991 | 1.887 | 1.755 | 1.646 |
| SEV (C) | 3.633 | 3.371 | 2.785 | 2.667 | 2.563 | 2.364 | 3.655 | 3.280 | 2.892 | 2.818 | 2.525 | 2.416 |
| $r^2$ | 0.828 | 0.816 | 0.813 | 0.802 | 0.819 | 0.851 | 0.823 | 0.807 | 0.810 | 0.844 | 0.818 | 0.823 |
| Bias | 2.140 | 1.970 | 1.610 | 1.520 | 1.430 | 1.330 | 2.160 | 1.910 | 1.680 | 1.460 | 1.420 | 1.340 |
| Bias CL | 4.585 | 4.219 | 3.444 | 3.254 | 3.064 | 2.858 | 4.621 | 4.089 | 3.601 | 3.123 | 3.034 | 2.872 |
| SEP (C) | 4.640 | 4.270 | 3.480 | 3.290 | 3.100 | 2.890 | 4.680 | 4.140 | 3.640 | 3.160 | 3.070 | 2.910 |
| Slope | 0.960 | 0.971 | 0.906 | 0.862 | 0.867 | 0.864 | 0.937 | 0.927 | 0.882 | 0.935 | 0.881 | 0.841 |
| Intercept | 2.120 | 1.280 | 4.530 | 7.230 | 7.380 | 7.610 | 3.490 | 3.660 | 5.790 | 3.260 | 6.140 | 8.660 |
| R.S.D. | 2.978 | 3.002 | 3.088 | 2.952 | 2.681 | 2.922 | 3.023 | 2.742 | 2.959 | 2.846 | 0.231 | 0.239 |
| \|Bias\| − Bias CL | −2.445 | −2.49 | −1.834 | −1.734 | −1.634 | −1.528 | −2.461 | −2.179 | −1.921 | −1.663 | −1.614 | −1.532 |
| \|Bias\| < Bias CL? | Yes | Yes | Yes | Yes | Yes | Yes | Yes | Yes | Yes | Yes | Yes | Yes |

TABLE 4c

Calibration and validation statistics (multivariate regressions)

| | PCR | | PLS | | MPLS | |
|---|---|---|---|---|---|---|
| | 2, 5, 5 | 2, 10, 10 | 2, 5, 5 | 2, 10, 10 | 2, 5, 5 | 2, 10, 10 |
| Energy required to shear | | | | | | |
| $R^2$ | 0.847 | 0.752 | 0.639 | 0.601 | 0.601 | 0.582 |
| SEC | 1.036 | 1.290 | 1.545 | 1.624 | 1.550 | 1.586 |
| SEC CL | 1.199 | 1.493 | 1.788 | 1.879 | 1.793 | 1.835 |
| SECV | 1.750 | 1.592 | 1.788 | 1.933 | 1.600 | 1.583 |
| $r^2$ | 0.5441 | 0.4876 | 0.4938 | 0.4157 | 0.3080 | 0.3563 |
| Bias | 0.620 | 0.770 | 0.930 | 0.970 | 0.930 | 0.950 |
| Bias CL | 1.331 | 1.658 | 1.986 | 2.087 | 1.992 | 2.038 |
| SEP (C) | 1.350 | 1.680 | 2.010 | 2.110 | 2.020 | 2.060 |
| Slope | 0.6540 | 0.6850 | 0.7390 | 0.6270 | 0.5220 | 0.6000 |
| Intercept | 5.2900 | 4.8100 | 3.7500 | 5.4500 | 7.3100 | 6.0200 |
| R.S.D. | 1.671 | 1.776 | 1.761 | 1.892 | 2.065 | 1.992 |
| \|Bias\| − Bias CL | −0.711 | −0.888 | −1.056 | −1.117 | −1.062 | −1.088 |
| \|Bias\| < Bias CL? | Yes | Yes | Yes | Yes | Yes | Yes |
| Energy required to comminute | | | | | | |
| $R^2$ | 0.584 | 0.574 | 0.605 | 0.595 | 0.556 | 0.558 |
| SEC | 23.378 | 23.682 | 22.788 | 23.075 | 24.164 | 24.101 |
| SEC CL | 27.048 | 27.400 | 26.366 | 26.698 | 27.958 | 27.885 |
| SECV | 26.030 | 26.121 | 25.548 | 25.683 | 26.409 | 26.252 |
| $r^2$ | 0.349 | 0.337 | 0.332 | 0.325 | 0.33 | 0.328 |
| Bias | 14.030 | 14.210 | 13.670 | 13.840 | 14.500 | 14.460 |
| Bias CL | 30.044 | 30.435 | 29.286 | 29.655 | 31.055 | 30.974 |
| SEP (C) | 30.390 | 30.790 | 29.620 | 30.000 | 31.410 | 31.330 |
| Slope | 0.649 | 0.636 | 0.644 | 0.632 | 0.657 | 0.638 |
| Intercept | 37.3 | 39.2 | 38.1 | 39.7 | 36.6 | 39.1 |
| R.S.D. | 28.246 | 28.676 | 28.714 | 28.884 | 28.651 | 28.900 |
| \|Bias\| − Bias CL | −16.014 | −16.225 | −15.616 | −15.815 | −16.555 | −16.514 |
| \|Bias\| < Bias CL? | Yes | Yes | Yes | Yes | Yes | Yes |
| Energy required to compress | | | | | | |
| $R^2$ | 0.251 | 0.160 | 0.231 | 0.208 | 0.038 | 0.040 |
| SEC | 0.225 | 0.241 | 0.265 | 0.269 | 0.260 | 0.260 |
| SEC CL | 0.260 | 0.279 | 0.307 | 0.311 | 0.301 | 0.301 |
| SECV | 0.299 | 0.277 | 0.301 | 0.307 | 0.301 | 0.299 |
| $r^2$ | 0.0220 | 0.0120 | 0.0130 | 0.0090 | 0.0060 | 0.0080 |
| Bias | 0.140 | 0.140 | 0.160 | 0.160 | 0.160 | 0.160 |
| Bias CL | 0.289 | 0.310 | 0.341 | 0.346 | 0.334 | 0.334 |
| SEP (C) | 0.290 | 0.310 | 0.340 | 0.350 | 0.340 | 0.340 |
| Slope | 0.2290 | 0.2270 | 0.1530 | 0.1330 | 0.2290 | 0.2590 |
| Intercept | 2.8900 | 2.9000 | 3.1700 | 3.2500 | 2.8900 | 2.7700 |
| R.S.D. | 0.235 | 0.236 | 0.236 | 0.237 | 0.237 | 0.237 |
| \|Bias\| − Bias CL | −0.149 | −0.170 | −0.181 | −0.186 | −0.174 | −0.174 |
| \|Bias\| < Bias CL? | Yes | Yes | Yes | Yes | Yes | Yes |

TABLE 4c-continued

Calibration and validation statistics (multivariate regressions)

| | PCR | | PLS | | MPLS | |
|---|---|---|---|---|---|---|
| | 2, 5, 5 | 2, 10, 10 | 2, 5, 5 | 2, 10, 10 | 2, 5, 5 | 2, 10, 10 |
| Digestibility of dry matter in vivo | | | | | | |
| $R^2$ | 0.909 | 0.900 | 0.958 | 0.937 | 0.571 | 0.892 |
| SEC | 1.638 | 1.711 | 1.109 | 1.356 | 3.756 | 1.911 |
| SEC CL | 1.895 | 1.980 | 1.283 | 1.569 | 4.346 | 2.211 |
| SECV | 2.159 | 2.075 | 1.957 | 1.776 | 3.797 | 2.180 |
| $r^2$ | 0.9022 | 0.8865 | 0.8447 | 0.8457 | 0.6963 | 0.8671 |
| Bias | 0.980 | 1.030 | 0.670 | 0.810 | 2.250 | 1.150 |
| Bias CL | 2.105 | 2.199 | 1.425 | 1.743 | 4.827 | 2.456 |
| SEP (C) | 2.130 | 2.220 | 1.440 | 1.760 | 4.880 | 2.480 |
| Slope | 0.848 | 0.807 | 0.839 | 0.822 | 0.981 | 0.745 |
| Intercept | 8.77 | 11.1 | 8.65 | 9.41 | 1.99 | 14.6 |
| R.S.D. | 1.704 | 1.834 | 2.143 | 2.139 | 2.914 | 1.984 |
| \|Bias\| − Bias CL | −1.125 | −1.169 | −0.755 | −0.933 | −2.577 | −1.306 |
| \|Bias\| < Bias CL? | Yes | Yes | Yes | Yes | Yes | Yes |
| Digestibility of dry matter in vitro | | | | | | |
| $R^2$ | 0.820 | 0.790 | 0.780 | 0.760 | 0.420 | 0.490 |
| SEC | 2.880 | 3.100 | 3.330 | 3.470 | 5.380 | 4.850 |
| SEC CL | 3.332 | 3.587 | 3.853 | 4.015 | 6.225 | 5.611 |
| SECV | 3.170 | 3.560 | 3.830 | 3.900 | 5.690 | 4.780 |
| $r^2$ | 0.8120 | 0.7730 | 0.8530 | 0.8040 | 0.6910 | 0.6690 |
| Bias | 1.730 | 1.860 | 2.000 | 2.080 | 3.230 | 2.910 |
| Bias CL | 3.701 | 3.984 | 4.280 | 4.459 | 6.914 | 6.233 |
| SEP (C) | 3.740 | 4.030 | 4.330 | 4.510 | 6.990 | 6.310 |
| Slope | 0.9180 | 0.9840 | 0.9530 | 0.6120 | 1.1200 | 0.8650 |
| Intercept | 3.4700 | −0.3600 | 2.3100 | 4.6300 | −7.5100 | 6.1800 |
| R.S.D. | 3.053 | 3.363 | 2.836 | 3.089 | 3.911 | 4.002 |
| \|Bias\| − Bias CL | −1.971 | −2.124 | −2.280 | −2.379 | −3.684 | −3.323 |
| \|Bias\| < Bias CL? | Yes | Yes | Yes | Yes | Yes | Yes |

TABLE 5

Standard error of laboratory determination (SEL)

| | Energy required to shear (kJ/m²) | Energy required to comminute (kJ/kg DM) | Energy required to compress (kJ/kg DM) | Digestibility of dry matter in vivo (%) | Digestibility of dry matter in vitro (%) |
|---|---|---|---|---|---|
| Mean SEL (n = 65) | 0.796 | 5.830 | 0.078 | not available | 0.314 |
| Median SEL | 0.788 | 5.492 | 0.085 | not available | 0.270 |
| Maximum SEL | 2.044 | 13.098 | 0.211 | not available | 1.126 |
| Minimum SEL | 0.114 | 0.780 | 0.019 | not available | 0.005 |
| SEL CL (using mean SEL) | 1.035 | 7.319 | 0.101 | not available | 0.408 |
| SEL CL (using median SEL) | 1.024 | 7.140 | 0.111 | not available | 0.351 |

TABLE 6a

Components of possible prediction equations from stepwise and step-up regression analyses.

| | Coefficient | Wavelength | Coefficient | Wavelength |
|---|---|---|---|---|
| | Energy required to shear | | | |
| Regression analysis | Stepwise | | Step-up | |
| Mathematical treatment | 2, 2, 2 (6 terms) | | 2, 5, 5 (2 terms) | |
| | 19.95 | | 28.09 | |
| | 2452.05 | 2048 | 1035.77 | 2048 |
| | −4255.81 | 1598 | 700.12 | 1958 |
| | 3823.49 | 1458 | | |

TABLE 6a-continued

Components of possible prediction equations
from stepwise and step-up regression analyses.

| Coefficient | Wavelength | Coefficient | Wavelength |
|---|---|---|---|
| −5319.88 | 1718 | | |
| 5148.38 | 1828 | | |
| 10239.46 | 1168 | | |

| | Energy required to compress | | |
|---|---|---|---|
| Regression analysis | Stepwise | | Step-up |
| Mathematical treatment | 2, 10, 10 (4 terms) | | 2, 10, 5 (3 terms) |

| Coefficient | Wavelength | Coefficient | Wavelength |
|---|---|---|---|
| −0.71 | | 2.49 | |
| −28.02 | 2278 | −31.05 | 1728 |
| 112.57 | 1588 | −108.89 | 1548 |
| −79.48 | 1728 | −105.95 | 1268 |
| | −911.04 | 1268 | |

| | Energy required to comminute | | |
|---|---|---|---|
| Regression analysis | Stepwise | | Step-up |
| Mathematical treatment | 2, 10, 5 (4 terms) | | 2, 10, 5 (1 term) |

| Coefficient | Wavelength | Coefficient | Wavelength |
|---|---|---|---|
| 231.42 | | 49.16 | |
| −3005.37 | 2128 | −1521.33 | 2268 |
| 4290.19 | 2408 | | |
| −4955.12 | 2018 | | |
| 18224.74 | 1138 | | |

| | Digestibility of dry matter in vivo | | |
|---|---|---|---|
| Regression analysis | Stepwise | | Step-up |
| Mathematical treatment | 2, 5, 5 (6 terms) | | 2, 10, 5 (3 terms) |

| Coefficient | Wavelength | Coefficient | Wavelength |
|---|---|---|---|
| 48.62 | | 49.15 | |
| −387.08 | 1918 | −612.43 | 1698 |
| −8799.69 | 1238 | 252.82 | 1418 |
| 8152.72 | 1158 | −943.77 | 1618 |
| 1249.01 | 1668 | | |
| 519.46 | 1908 | | |
| −181.84 | 2248 | | |

| | Digestibility of dry matter in vitro | | |
|---|---|---|---|
| Regression analysis | Stepwise | | Step-up |
| Mathematical treatment | 2, 2, 5 (5 terms) | | 2, 10, 10 (4 terms) |

| Coefficient | Wavelength | Coefficient | Wavelength |
|---|---|---|---|
| 63.43 | | 54.29 | |
| −558.01 | 1918 | −1171.70 | 1698 |
| 981.30 | 1908 | 311.12 | 1418 |
| −2186.89 | 1898 | −2657.69 | 1618 |
| 2003.05 | 2158 | −2319.81 | 1228 |
| −1491.99 | 1748 | | |

TABLE 6b

Components of possible prediction equations from multivariate regression analyses.

| Energy required to shear PCR (2,5,5) | | Energy required to compress PCR (2,5,5) | | Energy required to comminute PCR (2,5,5) | | PLS (2,5,5) | |
|---|---|---|---|---|---|---|---|
| Coefficient | Wavelength | Coefficient | Wavelength | Coefficient | Wavelength | Coefficient | Wavelength |
| −3.33 | | 3.35 | | −22.8 | | −16.44 | |
| 18.1 | 1108 | 0.17 | 1108 | 93.07 | 1108 | 91.01 | 1108 |
| 1.76 | 1118 | 0.02 | 1118 | 6.5 | 1118 | 7.19 | 1118 |
| −0.2 | 1128 | −0.01 | 1128 | −7.27 | 1128 | −5.63 | 1128 |
| −0.84 | 1138 | −0.01 | 1138 | −0.79 | 1138 | −0.13 | 1138 |
| 1.15 | 1148 | 0.01 | 1148 | 3.98 | 1148 | 5.58 | 1148 |
| −0.85 | 1158 | −0.01 | 1158 | −10.39 | 1158 | −8.55 | 1158 |
| 0.13 | 1168 | 0 | 1168 | −4.8 | 1168 | −4.72 | 1168 |
| 0.64 | 1178 | 0.03 | 1178 | 13.75 | 1178 | 13.27 | 1178 |
| −0.04 | 1188 | 0.04 | 1188 | 19.07 | 1188 | 17.38 | 1188 |
| −0.84 | 1198 | 0 | 1198 | 5.06 | 1198 | 0.44 | 1198 |

TABLE 6b-continued

Components of possible prediction equations from multivariate regression analyses.

| | | | | | | | |
|---|---|---|---|---|---|---|---|
| −1.14 | 1208 | −0.03 | 1208 | −8.92 | 1208 | −13.96 | 1208 |
| −1.71 | 1218 | −0.05 | 1218 | −20.83 | 1218 | −23.8 | 1218 |
| −1.73 | 1228 | −0.04 | 1228 | −17.9 | 1228 | −15.15 | 1228 |
| −0.85 | 1238 | −0.01 | 1238 | −3.26 | 1238 | −0.82 | 1238 |
| 0.12 | 1248 | 0 | 1248 | −0.85 | 1248 | 1.6 | 1248 |
| 0.5 | 1258 | 0 | 1258 | −2.55 | 1258 | −0.82 | 1258 |
| −0.9 | 1268 | −0.01 | 1268 | −4.67 | 1268 | −3.84 | 1268 |
| −1.25 | 1278 | 0 | 1278 | 1.29 | 1278 | 1.1 | 1278 |
| −0.25 | 1288 | 0.01 | 1288 | 5.24 | 1288 | 4.93 | 1288 |
| 0.2 | 1298 | 0.02 | 1298 | 5.9 | 1298 | 7.12 | 1298 |
| −0.1 | 1308 | 0.03 | 1308 | 9.22 | 1308 | 10.4 | 1308 |
| −0.66 | 1318 | 0.04 | 1318 | 14.26 | 1318 | 16.14 | 1318 |
| 1.25 | 1328 | 0.06 | 1328 | 22.7 | 1328 | 23.58 | 1328 |
| 5 | 1338 | 0.07 | 1338 | 27.63 | 1338 | 27.65 | 1338 |
| 2.34 | 1348 | 0.03 | 1348 | 6.64 | 1348 | 10.27 | 1348 |
| −2.37 | 1358 | −0.06 | 1358 | −26.23 | 1358 | −24.35 | 1358 |
| −10.62 | 1368 | −0.15 | 1368 | −66.36 | 1368 | −60.7 | 1368 |
| −9.89 | 1378 | −0.01 | 1378 | −1.83 | 1378 | 2.2 | 1378 |
| −1.68 | 1388 | 0.16 | 1388 | 67.77 | 1388 | 67.91 | 1388 |
| 8.65 | 1398 | 0.3 | 1398 | 125.67 | 1398 | 115.99 | 1398 |
| 23.88 | 1408 | 0.49 | 1408 | 188.24 | 1408 | 174.79 | 1408 |
| 13.87 | 1418 | 0.2 | 1418 | 67.19 | 1418 | 62.69 | 1418 |
| −12.53 | 1428 | −0.37 | 1428 | −153.54 | 1428 | −139.99 | 1428 |
| −0.01 | 1438 | −0.39 | 1438 | −145.28 | 1438 | −137.82 | 1438 |
| −1.04 | 1448 | −0.21 | 1448 | −66.74 | 1448 | −75.27 | 1448 |
| 2.09 | 1458 | −0.13 | 1458 | −37.31 | 1458 | −47.38 | 1458 |
| −2.69 | 1468 | −0.11 | 1468 | −49.09 | 1468 | −48.54 | 1468 |
| −8.05 | 1478 | −0.14 | 1478 | −70.4 | 1478 | −59.94 | 1478 |
| −1.2 | 1488 | −0.06 | 1488 | −26.64 | 1488 | −26.06 | 1488 |
| −2.08 | 1498 | −0.01 | 1498 | −1.87 | 1498 | −3.2 | 1498 |
| −1.69 | 1508 | 0.01 | 1508 | 4.61 | 1508 | 3.33 | 1508 |
| 0.35 | 1518 | 0.07 | 1518 | 28.69 | 1518 | 26.91 | 1518 |
| 2.8 | 1528 | 0.12 | 1528 | 49.84 | 1528 | 48.03 | 1528 |
| −0.01 | 1538 | 0.08 | 1538 | 34.38 | 1538 | 33.02 | 1538 |
| −1.83 | 1548 | 0 | 1548 | −3.32 | 1548 | 0.49 | 1548 |
| −3.7 | 1558 | −0.04 | 1558 | −21.79 | 1558 | −17.62 | 1558 |
| −0.66 | 1568 | −0.01 | 1568 | −4.61 | 1568 | −3.35 | 1568 |
| −1.99 | 1578 | −0.04 | 1578 | −13.08 | 1578 | −15.39 | 1578 |
| −3.67 | 1588 | −0.09 | 1588 | −43.91 | 1588 | −40.21 | 1588 |
| −5.26 | 1598 | −0.07 | 1598 | −3.02 | 1598 | −32.77 | 1598 |
| 0.06 | 1608 | −0.01 | 1608 | −7.28 | 1608 | −5.93 | 1608 |
| 2.89 | 1618 | 0.04 | 1618 | 17.4 | 1618 | 15 | 1618 |
| 0.22 | 1628 | 0.09 | 1628 | 34.68 | 1628 | 33.13 | 1628 |
| −0.98 | 1638 | 0.13 | 1638 | 49.47 | 1638 | 48.83 | 1638 |
| 10.23 | 1648 | 0.1 | 1648 | 53.35 | 1648 | 44.32 | 1648 |
| 10.67 | 1658 | 0 | 1658 | −3.16 | 1658 | −2.24 | 1658 |
| 6.52 | 1668 | −0.22 | 1668 | −82.09 | 1668 | −80.94 | 1668 |
| −20.53 | 1678 | −0.07 | 1678 | −60.38 | 1678 | −38.22 | 1678 |
| −6.15 | 1688 | 0.15 | 1688 | 55.65 | 1688 | 60.49 | 1688 |
| 7.4 | 1698 | 0.06 | 1698 | 48.43 | 1698 | 42.6 | 1698 |
| 4.76 | 1708 | 0.06 | 1708 | 34.19 | 1708 | 27.79 | 1708 |
| −19.73 | 1718 | −0.09 | 1718 | −54.88 | 1718 | −46.36 | 1718 |
| −5.98 | 1728 | −0.13 | 1728 | −54.69 | 1728 | −69.44 | 1728 |
| 19.24 | 1738 | 0.15 | 1738 | 78.27 | 1738 | 63.67 | 1738 |
| 6.42 | 1748 | 0.19 | 1748 | 90.94 | 1748 | 91.13 | 1748 |
| −3.1 | 1758 | 0.06 | 1758 | 21.41 | 1758 | 20.27 | 1758 |
| −4.03 | 1768 | −0.1 | 1768 | −47.2 | 1768 | −48.58 | 1768 |
| −1.47 | 1778 | −0.11 | 1778 | −42.48 | 1778 | −39.05 | 1778 |
| −0.44 | 1788 | −0.09 | 1788 | −36.22 | 1788 | −33.03 | 1788 |
| 1.72 | 1798 | −0.01 | 1798 | −2.33 | 1798 | −3.76 | 1798 |
| 2.76 | 1808 | 0.05 | 1808 | 20.97 | 1808 | 18.41 | 1808 |
| −3.79 | 1818 | −0.01 | 1818 | −6.58 | 1818 | −5.17 | 1919 |
| −4.32 | 1828 | −0.07 | 1828 | −30.81 | 1828 | −26.5 | 1828 |
| −2.97 | 1838 | −0.05 | 1838 | −17.29 | 1838 | −17.64 | 1838 |
| 1.97 | 1848 | 0.03 | 1848 | 17.65 | 1848 | 15.59 | 1848 |
| −2.48 | 1858 | 0.06 | 1858 | 28.06 | 1858 | 28.11 | 1858 |
| −6.48 | 1868 | 0.08 | 1868 | 42.2 | 1868 | 40.46 | 1868 |
| −0.22 | 1878 | 0.23 | 1878 | 115.52 | 1878 | 108.98 | 1878 |
| −1.64 | 1888 | 0.44 | 1888 | 219.15 | 1888 | 208.1 | 1888 |
| 31.11 | 1898 | 0.2 | 1898 | 98.82 | 1898 | 99.42 | 1898 |
| 2.3 | 1908 | −0.35 | 1908 | −179.9 | 1908 | −157.11 | 1908 |
| −25.69 | 1918 | −0.47 | 1918 | −251.3 | 1918 | −220.58 | 1918 |
| −12.22 | 1928 | −0.34 | 1928 | −171.93 | 1928 | −172.09 | 1928 |
| 15.11 | 1938 | −0.14 | 1938 | −55.38 | 1938 | −77.27 | 1938 |
| 28.89 | 1948 | −0.03 | 1948 | −6.17 | 1948 | −23.21 | 1948 |
| 27.72 | 1958 | −0.04 | 1958 | −16.65 | 1958 | −19.03 | 1958 |
| 8.93 | 1968 | 0.05 | 1968 | 12.02 | 1968 | 22.46 | 1968 |

TABLE 6b-continued

Components of possible prediction equations from multivariate regression analyses.

| | | | | | | | |
|---|---|---|---|---|---|---|---|
| −15.33 | 1978 | 0.23 | 1978 | 68.03 | 1978 | 88.88 | 1978 |
| −9.25 | 1988 | 0.29 | 1988 | 85.84 | 1988 | 103.6 | 1988 |
| −3.33 | 1998 | 0.27 | 1998 | 78.68 | 1998 | 98.03 | 1998 |
| 1.28 | 2008 | 0.32 | 2008 | 97.53 | 2008 | 115.14 | 2008 |
| 20.22 | 2018 | 0.25 | 2018 | 104.79 | 2018 | 99.25 | 2018 |
| 18.34 | 2028 | 0.08 | 2028 | 42.08 | 2028 | 33.39 | 2028 |
| 9.58 | 2038 | −0.01 | 2038 | 23.98 | 2038 | 11.1 | 2038 |
| 5.59 | 2048 | 0.13 | 2048 | 101.85 | 2048 | 77.38 | 2048 |
| −8.64 | 2108 | −0.26 | 2108 | −108.06 | 2108 | −107.49 | 2108 |
| −6.28 | 2118 | −0.23 | 2118 | −91.06 | 2118 | −91.23 | 2118 |
| −4.49 | 2128 | −0.23 | 2128 | −97.55 | 2128 | −93.37 | 2128 |
| −16.58 | 2138 | −0.2 | 2138 | −101.35 | 2138 | −85.08 | 2138 |
| −9.08 | 2148 | −0.01 | 2148 | −13.78 | 2148 | −9.31 | 2148 |
| −2.68 | 2158 | 0.08 | 2158 | 37.5 | 2158 | 36.99 | 2158 |
| 3.19 | 2168 | 0.26 | 2168 | 118.43 | 2168 | 110.03 | 2168 |
| 4.27 | 2178 | 0.26 | 2178 | 122.68 | 2178 | 109.87 | 2178 |
| −6.3 | 2188 | 0.16 | 2188 | 54.73 | 2188 | 58.98 | 2188 |
| −13.33 | 2198 | 0.15 | 2198 | 38.08 | 2198 | 53.78 | 2198 |
| −2.74 | 2208 | 0.35 | 2208 | 129.58 | 2208 | 147.19 | 2208 |
| 35.77 | 2218 | 0.36 | 2218 | 171.77 | 2218 | 149.55 | 2218 |
| 30.36 | 2228 | 0.42 | 2228 | 182.8 | 2228 | 168.64 | 2228 |
| 22.91 | 2238 | 0.22 | 2238 | 73.19 | 2238 | 88.39 | 2238 |
| 98.61 | 2248 | −0.67 | 2248 | −152.9 | 2248 | −250.89 | 2248 |
| −15.77 | 2258 | −0.47 | 2258 | −184.5 | 2258 | −189.12 | 2258 |
| −85.22 | 2268 | −0.2 | 2268 | −167.23 | 2268 | −101.11 | 2268 |
| −35.1 | 2278 | −0.45 | 2278 | −214.87 | 2278 | −180.14 | 2278 |
| 27.27 | 2288 | 0.22 | 2288 | 148 | 2288 | 122.32 | 2288 |
| 4.27 | 2298 | 0.84 | 2298 | 352.88 | 2298 | 341.16 | 2298 |
| −13.06 | 2308 | 0.29 | 2308 | 78.88 | 2308 | 63.66 | 2308 |
| 0.67 | 2318 | −0.48 | 2318 | −208.27 | 2318 | −207.81 | 2318 |
| −13.34 | 2328 | −0.47 | 2328 | −167.95 | 2328 | −150.99 | 2328 |
| −23.3 | 2338 | −0.2 | 2338 | −79.26 | 2338 | −66.98 | 2338 |
| 0.66 | 2348 | 0.15 | 2348 | 62.44 | 2348 | 40.83 | 2348 |
| 7.98 | 2358 | −0.07 | 2358 | −23.09 | 2358 | −30.25 | 2358 |
| −15.62 | 2368 | 0.08 | 2368 | 25.53 | 2368 | 41.9 | 2368 |
| −16.39 | 2378 | 0.05 | 2378 | −3.86 | 2378 | 12.67 | 2378 |
| −4.44 | 2388 | −0.05 | 2388 | −33.15 | 2388 | −26.65 | 2388 |
| 21.16 | 2398 | 0.2 | 2398 | 98.53 | 2398 | 79.92 | 2398 |
| 49.9 | 2408 | 0.22 | 2408 | 130.87 | 2408 | 89.16 | 2408 |
| 22.34 | 2418 | 0.29 | 2418 | 120.05 | 2418 | 107.71 | 2418 |
| −1.47 | 2428 | 0.22 | 2428 | 72.57 | 2428 | 84.86 | 2428 |
| 17.19 | 2438 | 0.03 | 2438 | 6.72 | 2438 | 3.78 | 2438 |
| 15.21 | 2448 | 0.11 | 2448 | 55.93 | 2448 | 45.74 | 2448 |
| −14.12 | 2458 | 0.16 | 2458 | 59.89 | 2458 | 71.29 | 2458 |
| −24.15 | 2468 | −0.04 | 2468 | −31.79 | 2468 | −13.92 | 2468 |

| Digestibility of dry matter in vitro | | Digestibility of dry matter in vivo | | | |
|---|---|---|---|---|---|
| PLS (2,5,5) | | PCR (2,5,5) | | PLS (2,5,5) | |
| Coefficient | Wavelength | Coefficient | Wavelength | Coefficient | Wavelength |
| 59.77 | | 40.56 | | 63.64 | |
| −96.26 | 1108 | −161.5 | 1108 | −78.7 | 1108 |
| 7.55 | 1118 | 12.91 | 1118 | 4 | 1118 |
| 12.25 | 1128 | 22.04 | 1128 | 8.68 | 1128 |
| 6.85 | 1138 | 19.51 | 1138 | 3.94 | 1138 |
| 6.74 | 1148 | 8.19 | 1148 | 7.08 | 1148 |
| 11.89 | 1158 | 5.29 | 1158 | 6.24 | 1158 |
| 4.45 | 1168 | −0.92 | 1168 | 0.43 | 1168 |
| −10.08 | 1178 | −11.1 | 1178 | −5.6 | 1178 |
| −29.6 | 1188 | −37.4 | 1188 | −15.1 | 1188 |
| −20.43 | 1198 | −26.13 | 1198 | −10.61 | 1198 |
| −20.05 | 1208 | −38.03 | 1208 | −15.98 | 1208 |
| −15.65 | 1218 | −35.64 | 1218 | −13.18 | 1218 |
| 2.41 | 1228 | −13.39 | 1228 | 2.03 | 1228 |
| 6.62 | 1238 | 0.89 | 1238 | 6.37 | 1238 |
| 8.8 | 1248 | 14.13 | 1248 | 7.08 | 1248 |
| 7.47 | 1258 | 17.48 | 1258 | 5.09 | 1258 |
| −1.32 | 1268 | −7.44 | 1268 | −0.25 | 1268 |
| −7.39 | 1278 | −22.67 | 1278 | −4.08 | 1278 |
| −0.79 | 1288 | −1.05 | 1288 | 0.15 | 1288 |
| 3.48 | 1298 | 9.23 | 1298 | 3.72 | 1298 |
| 5.1 | 1308 | 13.17 | 1308 | 4.38 | 1308 |
| 8.23 | 1318 | 16.6 | 1318 | 6.03 | 1318 |
| 8.48 | 1328 | 25.91 | 1328 | 9.03 | 1328 |
| 17.78 | 1338 | 40.71 | 1338 | 13 | 1338 |

TABLE 6b-continued

Components of possible prediction equations from multivariate regression analyses.

| | | | | | |
|---:|---:|---:|---:|---:|---:|
| 24.61 | 1348 | 51.12 | 1348 | 13.51 | 1348 |
| −0.07 | 1358 | 4.6 | 1358 | 0.20 | 1358 |
| −23.89 | 1368 | −88.33 | 1368 | −13.81 | 1368 |
| −29.88 | 1378 | −68.78 | 1378 | −8.13 | 1378 |
| −18.97 | 1388 | 6.08 | 1388 | −1.4 | 1388 |
| 23.92 | 1398 | 32.14 | 1398 | 18.06 | 1398 |
| 60.7 | 1408 | 78.51 | 1408 | 32.08 | 1408 |
| 55.51 | 1418 | 90.64 | 1418 | 11.94 | 1418 |
| −0.3 | 1428 | −1.47 | 1428 | −14.78 | 1428 |
| −28.21 | 1438 | −11.15 | 1438 | −19.94 | 1438 |
| −32.57 | 1448 | 10.5 | 1448 | −19.24 | 1448 |
| −28.08 | 1458 | 18.31 | 1458 | −18.15 | 1458 |
| 1.48 | 1468 | −3.82 | 1468 | 3.7 | 1468 |
| 18.21 | 1478 | −18.48 | 1478 | 10.65 | 1478 |
| −0.65 | 1488 | −25.14 | 1488 | −0.75 | 1488 |
| −22.99 | 1498 | −74.43 | 1498 | −7.65 | 1498 |
| −23.44 | 1508 | −75.49 | 1508 | −9.41 | 1508 |
| −15.74 | 1518 | −58.78 | 1518 | −8.06 | 1518 |
| −9.09 | 1528 | −25.77 | 1528 | −5.21 | 1528 |
| −2.8 | 1538 | −7.83 | 1538 | −3.83 | 1538 |
| 10.62 | 1548 | 17.83 | 1548 | 4.58 | 1548 |
| 28.76 | 1558 | 52.96 | 1558 | 15.5 | 1558 |
| 5.02 | 1568 | 21.09 | 1588 | 15.5 | 1558 |
| −6.6 | 1578 | −27.42 | 1578 | −3.09 | 1578 |
| −18.09 | 1588 | −42.59 | 1588 | −5.77 | 1588 |
| −9.26 | 1598 | −63.69 | 1598 | −8.48 | 1598 |
| −6.66 | 1608 | −3.06 | 1608 | −0.65 | 1608 |
| −3.82 | 1618 | −1.82 | 1618 | −0.67 | 1618 |
| −3.58 | 1628 | −2.81 | 1628 | 0.24 | 1628 |
| 0.55 | 1638 | −9.18 | 1638 | 3.42 | 1638 |
| 0.5 | 1648 | 13.81 | 1648 | 0.66 | 1648 |
| 23.87 | 1658 | 61.39 | 1658 | 13.12 | 1658 |
| 54.92 | 1668 | 159.6 | 1668 | 28.91 | 1668 |
| 78.64 | 1678 | 101.05 | 1678 | 44.01 | 1678 |
| −13.9 | 1688 | −79.38 | 1688 | −8.19 | 1688 |
| −74.54 | 1698 | −77.73 | 1698 | −34 | 1698 |
| −38.63 | 1708 | −43.87 | 1708 | −18.38 | 1708 |
| −24.48 | 1718 | 21.34 | 1718 | 2.17 | 1718 |
| −17.91 | 1728 | −25.8 | 1728 | −31.77 | 1728 |
| −43.01 | 1738 | −40.51 | 1738 | −21.21 | 1738 |
| '29.25 | 1748 | −28.11 | 1748 | −5.24 | 1748 |
| −16.33 | 1758 | −4.55 | 1758 | −11.67 | 1758 |
| 0.43 | 1768 | 2.68 | 1768 | −0.49 | 1768 |
| 28.21 | 1778 | 20.91 | 1778 | 21.37 | 1778 |
| 18.92 | 1788 | 13.59 | 1788 | 13.25 | 1788 |
| 0.54 | 1798 | 9.35 | 1798 | −0.93 | 1798 |
| −2.44 | 1808 | 7.17 | 1808 | −4.5 | 1808 |
| −2.72 | 1818 | −15.30 | 1818 | −2.3 | 1818 |
| −5.84 | 1828 | −29.4 | 1828 | −3.37 | 1828 |
| −4.37 | 1838 | −16.21 | 1838 | −0.05 | 1838 |
| −8.79 | 1848 | 2.3 | 1848 | −2.23 | 1848 |
| −7.72 | 1858 | −0.87 | 1858 | −3.79 | 1858 |
| −29.93 | 1868 | −21.29 | 1868 | −9.61 | 1868 |
| −98.16 | 1878 | −82.33 | 1878 | −34.58 | 1878 |
| −116.18 | 1888 | −102.15 | 1888 | −52.89 | 1888 |
| 117.59 | 1898 | 211.27 | 1898 | 38.2 | 1898 |
| 185 | 1908 | 204.51 | 1908 | 68.78 | 1908 |
| 33.91 | 1918 | −3.12 | 1918 | 28.1 | 1918 |
| −35.31 | 1928 | 18.14 | 1928 | −3.79 | 1928 |
| −44.59 | 1938 | 35.39 | 1938 | −19.45 | 1938 |
| −9.28 | 1948 | −8.24 | 1948 | −8.41 | 1948 |
| 35.73 | 1958 | −11.32 | 1948 | 15.95 | 1958 |
| 28.56 | 1968 | −37.15 | 1968 | 13.49 | 1968 |
| 10.68 | 1978 | −44.28 | 1978 | 2.03 | 1978 |
| 10.98 | 1988 | −61.81 | 1988 | 0.57 | 1988 |
| 65.12 | 1998 | −72.2 | 1998 | 31.07 | 1998 |
| 83.13 | 2008 | −63.31 | 2008 | 38.57 | 2008 |
| 7.23 | 2018 | 37.37 | 2018 | −1.21 | 2018 |
| 0.99 | 2028 | 183.21 | 2028 | −9.38 | 2028 |
| −10.85 | 2038 | 156.66 | 2038 | −14.51 | 2038 |
| −84.48 | 2048 | −2.09 | 2048 | −54.72 | 2048 |
| −122.91 | 2058 | −178.03 | 2058 | −68.29 | 2058 |
| −35.85 | 2068 | −104.9 | 2068 | −1.09 | 2068 |
| 34.93 | 2078 | −7.7 | 2078 | 37.65 | 2078 |
| 28.83 | 2088 | 82.28 | 2088 | 27.17 | 2088 |
| 18.03 | 2098 | 54.28 | 2098 | 18.01 | 2098 |
| 5.09 | 2108 | 14.14 | 2108 | 15.52 | 2108 |

TABLE 6b-continued

Components of possible prediction equations from multivariate regression analyses.

| | | | | | |
|---|---|---|---|---|---|
| −9.58 | 2118 | −40.31 | 2118 | 7.88 | 2118 |
| 9.79 | 2128 | 2.34 | 2128 | 13.25 | 2128 |
| 23.04 | 2138 | 28.94 | 2138 | 18.49 | 2138 |
| −10.93 | 2148 | −31.56 | 2148 | −8.42 | 2148 |
| −10.97 | 2158 | 3.05 | 2158 | −9.12 | 2158 |
| −41.78 | 2168 | −68.48 | 2168 | −27.35 | 2168 |
| −46.69 | 2178 | −107.52 | 2178 | −32.56 | 2178 |
| −14.5 | 2188 | −54.54 | 2188 | −12.58 | 2188 |
| −0.14 | 2198 | −11.17 | 2198 | 4.5 | 2198 |
| −7.15 | 2208 | −2.14 | 2208 | 4.87 | 2208 |
| −48.05 | 2218 | −43.68 | 2218 | −30.89 | 2218 |
| −18.22 | 2228 | −0.01 | 2228 | −19.94 | 2228 |
| 88.33 | 2238 | 100.18 | 2238 | 14.80 | 2238 |
| −24.11 | 2248 | 53.32 | 2248 | −53.79 | 2248 |
| 55.09 | 2258 | 81.52 | 2258 | 18.08 | 2258 |
| 110.06 | 2268 | 48.93 | 2268 | 90.27 | 2268 |
| 52.18 | 2278 | −9.18 | 2278 | 83.96 | 2278 |
| −89.38 | 2288 | 25.1 | 2288 | −35.59 | 2288 |
| −109.09 | 2298 | −47.83 | 2298 | −77.98 | 2298 |
| −54.11 | 2308 | −23.3 | 2308 | −61.38 | 2308 |
| 17.63 | 2318 | −73.92 | 2318 | 22.34 | 2318 |
| 23.71 | 2328 | −23.74 | 2328 | 46.6 | 2328 |
| 62.19 | 2338 | 13.84 | 2338 | 37.70 | 2338 |
| −58.18 | 2348 | −21.67 | 2348 | −48.16 | 2348 |
| −21.28 | 2358 | −77.29 | 2358 | −7.88 | 2358 |
| 4.01 | 2368 | −88.75 | 2368 | 18.34 | 2368 |
| 32.53 | 2378 | 28.42 | 2378 | 17.8 | 2378 |
| 35.58 | 2388 | 68.01 | 2388 | 1.95 | 2388 |
| −21.25 | 2398 | 22.17 | 2398 | −27.54 | 2398 |
| −70.01 | 2408 | −28.96 | 2408 | −50.39 | 2408 |
| −18.88 | 2418 | 8.02 | 2418 | −18.09 | 2418 |
| 61.66 | 2428 | 75.99 | 2428 | 17.75 | 2428 |
| 14.94 | 2438 | 58.83 | 2438 | −3.66 | 2438 |
| −11.88 | 2448 | 8.46 | 2448 | −11.21 | 2448 |
| 5.35 | 2458 | −4.33 | 2458 | 3.97 | 2458 |
| 10.49 | 2468 | −33.25 | 2468 | 11.29 | 2468 |

TABLE 7

Descriptions of forages used in Table 8.

| Sample in Table 8 | Genus | Species | Variety | Common name | Part of plant | Process undergone | Stage of maturity | Regrowth |
|---|---|---|---|---|---|---|---|---|
| 1 | Panicum | *coloratum* | Kabutabula CPI 16796 | Makarikari grass | aerial | dried and chaffed | mid bloom (9 weeks' regrowth) | mid bloom - regrowth |
| 2 | Pancium | *maximum* | Colonlao | Guinea grass | aerial | dreid and chaffed | vegetative regrowth (4 weeks') | vegetative regrowth |
| 3 | Pancium | *coloratum* | Babbalsi | Makarlkari grass | aerial | dried and chaffed | mid bloom (1 month's regrowth) | mid bloom - regrowth |
| 4 | Pancium | *maximum* | Hamii | Guinea grass | aerial | dried and chaffed | early bloom (1 month's regrowth) | early bloom - regrowth |
| 5 | Pancium | *coloratum* var Makeri-kariense | Burnett | Makarikari grass | aerial | dried and chaffed | mid bloom (6 weeks' regrowth) | mid bloom - regrowth |
| 6 | Pancium | *maximum* var. tricho-glume | Petrie | Green Panic | aerial | dried and chaffed | mid bloom (4 weeks' regrowth) | mid bloom - regrowth |

TABLE 8

Examples of energy required to shear, digestibility of dry matter in vivo,
forage consumption constraint (FCC), and voluntary feed consumption (VFC)

| Sample in Table 7 | Energy required to shear, predicted using NIR[1] (kJ/m$^2$) | Digestibility of dry matter in vivo, predicted using NIR[2] (%) | Predicted FCC[3] (g OM/d/MBW)[4] | Predicted VFC[5] (g OM/d/MBW) | Actual VFC (g OM/d/MBW) | Actual VFC (g OM/d) |
|---|---|---|---|---|---|---|
| 1 | 20.51 | 51.29 | 86.85 | 32.52 | 30.77 | 534 |
| 2 | 16.70 | 54.73 | 66.92 | 44.95 | 39.47 | 686 |
| 3 | 13.75 | 56.69 | 51.49 | 56.51 | 48.79 | 848 |
| 4 | 13.18 | 59.59 | 48.41 | 54.34 | 53.58 | 931 |
| 5 | 17.52 | 65.18 | 71.21 | 39.74 | 43.66 | 759 |
| 6 | 16.63 | 55.88 | 66.55 | 43.01 | 45.66 | 793 |

[1]Predicted using the calibration equation from stepwise regression analysis (Table 6a).
[2]Predicted using the calibration equation from stepwise regression analysis (Table 6a).
[3]Predicted using predicted energy required to shear, and the relationship between energy required to shear and FCC.
[4]Calculated from predicted FCC and predicted digestibility of dry matter in vivo.
[5]Abbreviations used: organic matter (OM), metabolic body weight (MBW) = BW$^{0.75}$ The claims of the invention are as follows:

1. A method for determining a biomechanical property of a feed, the biomechanical property being one that reflects how easy it is for an animal to chew the feed, the method comprising the steps of:
   (a) subjecting the feed to infrared radiation to obtain spectral data; and
   (b) using the spectral data to determine the biomechanical property; whereby, the biomechanical property of the feed is determined on the basis of the bond energies of the chemical constituents of the feed.

2. A method according to claim 1 wherein the biomechanical property is selected from the group comprising; shear energy, compression energy, communication energy, tensile strength, shear strength and intrinsic shear strength.

3. A method according to claim 1 wherein the biomechanical property of the feed is determined directly from the spectral data.

4. A method according to claim 1 wherein the spectral data is used to determine another property of the feed and the other property is used to determine the biomechanical property on the basis of a correlation between the other property and the biomechanical property.

5. A method according to claim 4 wherein the other property is ADF content, NDF content or lignin content.

6. A method according to claim 1 wherein the spectral data is a reflectance spectrum over a predetermined range of wavelengths.

7. A method according to claim 6 wherein the predetermined range is approximately 700 nm to 3000 nm.

8. A method according to claim 6 wherein the predetermined range is approximately 1100 nm to 2500 nm.

9. A method according to claim 6 wherein the data obtained for the spectral range of approximately 1850 nm to 1970 nm is disregarded.

10. A method according to claim 6 wherein the spectral data is recorded at 2 nm intervals over the predetermined range.

11. A method according to claim 1 wherein the spectral data is a reflectance spectrum and a reflectance reading is taken at a combination of wavelengths.

12. A method according to claim 11 wherein the combination of wavelengths is selected from the group comprising: 1168 nm, 1458 nm, 1598 nm, 1718 nm, 1828 nm, 2048 nm, 1138 nm, 2018 nm, 2128 nm, 2408 nm, 1268 nm, 1588 nm, 1728 nm, 2278 nm, 1158 nm, 1238 nm, 1668 nm, 1908 nm, 2248 nm, 1698 nm, 1748 nm, 1918 nm and 2158 nm.

13. A method according to claim 11 wherein the combination of wavelengths is 1168 nm, 1458 nm, 1598 nm, 1718 nm, 1828 nm and 2048 nm and the biomechanical property is shear energy.

14. A method according to claim 11 wherein the combination of wavelengths is 1268 nm, 1588 nm, 1728 nm and 2278 nm and the biomechanical property is compression energy.

15. A method according to claim 11 wherein the combination of wavelengths is 1138 nm, 2018 nm, 2128 nm and 2408 nm and the biomechanical property is comminution energy.

16. A method for determining a biomechanical property of a feed, the biomechanical property being one that reflects how easy it is for an animal to chew the feed, the method comprising the steps of:
   (a) subjecting the feed to infrared radiation to obtain spectral data; and
   (b) comparing the spectral data obtained in (a) with a calibration equation to determine the biomechanical property;
whereby, the biomechanical property of the feed is determined on the basis of the bond energies of the chemical constituents of the feed.

17. A method according to claim 16 wherein the calibration equation is $y_1 = 19.95 + 10239.46 R_{1168} + 3623.49 R_{1458} - 4255.61 R_{1598} - 5319.88 R_{1718} + 5148.38 R_{1828} + 2452.05 R_{2048}$ and the biomechanical property is shear energy ($y_1$).

18. A method according to claim 16 wherein the calibration equation is $y_2 = 231.42 + 18224.74 R_{1138} - 4955.12 R_{2018} - 3005.37 R_{2128} + 4290.18 R_{2408}$ and the biomechanical property is comminution energy ($y_2$).

19. A method according to claim 16 wherein the calibration equation is $y_3 = -0.71'911.04 R_{1268} + 112.57 R_{1588} - 79.48 R_{1728} - 28.02 R2278$ and the biomechanical property is compression energy ($y_3$).

20. A method according to claim 16 wherein the calibration equation is determined from laboratory data establishing a correlation between reflectance and the biomechanical property.

21. A method according to claim 1 wherein an additional property of the feed is also determined.

22. A method according to claim 21 wherein the additional property of the feed is digestibility of dry matter in vivo or in vitro.

23. A method for determining feed quality, the method comprising the steps of:

(a) subjecting the feed to infrared radiation to obtain spectral data;
(b) using the spectral data to determine a biomechanical property of the feed, the biomechanical property being one that reflects how easy it is for an animal to chew the feed; and
(c) using the biomechanical property obtained in step (b) to determine feed quality;

whereby, the biomechanical property of the feed and thus feed quality is determined on the basis of the bond energies of the chemical constituents of the feed.

24. A method according to claim 23 wherein the feed quality is determined as a measure of voluntary feed consumption (VFC).

25. A method according to claim 23 wherein the feed quality is determined as a measure of forage consumption constraint (FCC).

26. A spectrometer configured to carry out the method according to claim 1 wherein the spectrometer is adapted to receive a sample of feed and determine a biomechanical property of the feed.

27. A spectrometer configured to carry out the method according to claim 23 wherein the spectrometer is adapted to receive a sample of feed and determine the quality of the feed.

28. A spectrometer according to claim 26 further comprising a data processing means for determining the biomechanical property or the quality of the feed.

* * * * *